US010894985B2

(12) United States Patent
Doucette-Stamm et al.

(10) Patent No.: US 10,894,985 B2
(45) Date of Patent: *Jan. 19, 2021

(54) METHODS FOR PREDICTING RESPONSE TO TREATMENT

(71) Applicant: Sitokine Limited, London (GB)

(72) Inventors: Lynn Doucette-Stamm, Framingham, MA (US); Gordon W. Duff, Sheffield (GB); Kenneth S. Kornman, Newton, MA (US)

(73) Assignee: Sitokine Limited, London (GB)

( * ) Notice: Subject to any disclaimer, the term of this patent is extended or adjusted under 35 U.S.C. 154(b) by 462 days.

This patent is subject to a terminal disclaimer.

(21) Appl. No.: 15/404,733

(22) Filed: Jan. 12, 2017

(65) Prior Publication Data

US 2017/0198350 A1     Jul. 13, 2017

Related U.S. Application Data

(60) Provisional application No. 62/277,760, filed on Jan. 12, 2016.

(51) Int. Cl.
| | | |
|---|---|---|
| *C12Q 1/68* | (2018.01) | |
| *C12Q 1/6883* | (2018.01) | |
| *G16B 30/00* | (2019.01) | |
| *A61K 9/00* | (2006.01) | |
| *A61K 38/16* | (2006.01) | |

(52) U.S. Cl.
CPC .......... *C12Q 1/6883* (2013.01); *A61K 9/0048* (2013.01); *A61K 38/16* (2013.01); *G16B 30/00* (2019.02); *C12Q 2600/106* (2013.01); *C12Q 2600/112* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 4,988,167 A | 1/1991 | Fergason |
| 4,988,617 A | 1/1991 | Landegren |
| 5,118,801 A | 6/1992 | Lizardi |
| 5,210,015 A | 5/1993 | Gelfand |
| 5,270,184 A | 12/1993 | Walker |
| 5,312,728 A | 5/1994 | Lizardi |
| 5,399,491 A | 3/1995 | Kacian |
| 5,422,252 A | 6/1995 | Walker |
| 5,494,810 A | 2/1996 | Barany |
| 5,498,531 A | 3/1996 | Jarrell |
| 5,527,675 A | 6/1996 | Coull |
| 5,538,848 A | 7/1996 | Livak |
| 5,539,082 A | 7/1996 | Nielsen |
| 5,623,049 A | 4/1997 | Lobberding |
| 5,686,246 A | 11/1997 | Kornman |
| 5,698,399 A | 12/1997 | Duff |
| 5,714,331 A | 2/1998 | Vaerlose |
| 5,808,918 A | 9/1998 | Fink |
| 5,830,711 A | 11/1998 | Barany |
| 5,866,336 A | 2/1999 | Nazarenko |
| 6,027,889 A | 2/2000 | Barany |
| 6,027,923 A | 2/2000 | Wallace |
| 6,054,564 A | 4/2000 | Barany |
| 6,108,635 A | 8/2000 | Herren |
| 6,117,635 A | 9/2000 | Nazarenko |
| 6,140,047 A | 10/2000 | Duff |
| 6,210,877 B1 | 4/2001 | Francis |
| 6,251,598 B1 | 6/2001 | Di Giovine |
| 6,268,142 B1 | 7/2001 | Duff |
| 6,268,148 B1 | 7/2001 | Barany |
| 6,383,775 B1 | 5/2002 | Duff |
| 6,437,216 B1 | 8/2002 | Duff |
| 6,524,795 B1 | 2/2003 | Francis |
| 6,551,785 B2 | 4/2003 | Di Giovine |
| 6,558,905 B1 | 5/2003 | Van Dijk |
| 6,706,478 B2 | 3/2004 | Duff |

(Continued)

FOREIGN PATENT DOCUMENTS

| | | |
|---|---|---|
| EP | 235726 | 9/1987 |
| WO | WO 89/11548 | 11/1989 |

(Continued)

OTHER PUBLICATIONS

<https://clinicaltrials.gov/ct2/show/study/NCT02160899>, Clinical Trials, Identifier NCT02160899, U.S. National Library of Medicine, Jun. 11, 2014, 18 pages.
Bailly, S. et al., "Genetic polymorphism of human interleukin-1 alpha," Eur J Immunol 23:1240-1245 (1993).
Bailly, S. et al., "Polymorphic tandem repeat region in interleukin-1 alpha intron 6," Hum Genet 91:85-86 (1993).
Bailly, S. et al., "An intronic polymorphic repeat sequence modulates interleukin-1 alpha gene regulation," Mol Immunol 33:999-1006 (1996).

(Continued)

*Primary Examiner* — Jehanne S Sitton

(74) *Attorney, Agent, or Firm* — Cooley LLP; Cynthia A. Kozakiewicz; Ivor R. Elrifi

(57) ABSTRACT

The present invention provides stratification methods and kits to identify whether an individual having an inflammation-related disorder has genotype-specific differential expression of IL-1, i.e., is a "high" or "low" producer of IL-1, such that s/he can be provided an appropriate anti-inflammatory drug and at an appropriate dose. The stratification of high or low IL-1 producers is used to guide assignment of different drug doses and therefore reduce drug toxicity and adverse events in an individual who, without stratification, may be prescribed a higher dose than needed to manage the primary indication. The use of IL-1 stratification of drug dosing would allow a better clinical benefit-risk appraisal in an individual patient.

13 Claims, 2 Drawing Sheets

(56) References Cited

U.S. PATENT DOCUMENTS

| | | | |
|---|---|---|---|
| 6,713,253 B1 | 3/2004 | Duff | |
| 6,720,141 B1 | 4/2004 | Crossman | |
| 6,730,476 B1 | 5/2004 | Duff | |
| 6,733,967 B1 | 5/2004 | Kornman | |
| 6,746,839 B1 | 6/2004 | Duff | |
| 7,723,028 B2 | 5/2010 | Kornman | |
| 7,820,383 B2 | 10/2010 | Francis | |
| 8,101,360 B2 | 1/2012 | Kornman | |
| 8,105,775 B2 | 1/2012 | Kornman | |
| 9,347,090 B2 | 5/2016 | Kornman et al. | |
| 10,329,620 B2 | 6/2019 | Kornman et al. | |
| 10,337,070 B2 | 7/2019 | Kornman et al. | |
| 2002/0182612 A1 | 12/2002 | Duff | |
| 2003/0100031 A1 | 5/2003 | Dower | |
| 2003/0124524 A1 | 7/2003 | Kornman | |
| 2003/0152947 A1 | 8/2003 | Crossman | |
| 2003/0175764 A1 | 9/2003 | Francis | |
| 2003/0235890 A1 | 12/2003 | Wyllie | |
| 2004/0110168 A1 | 6/2004 | Van Dijk | |
| 2004/0152124 A1 | 8/2004 | Duff | |
| 2005/0032077 A1 | 2/2005 | Duff | |
| 2005/0064453 A1 | 3/2005 | Duff | |
| 2005/0171338 A1 | 8/2005 | Dower | |
| 2005/0282198 A1 | 12/2005 | Duff | |
| 2006/0183161 A1 | 8/2006 | Nicklin | |
| 2006/0252050 A1 | 11/2006 | Ordovas | |
| 2007/0264645 A1 | 11/2007 | Kornman | |
| 2007/0275104 A1 | 11/2007 | Kornman | |
| 2008/0118920 A1 | 5/2008 | Duff | |
| 2008/0187920 A1 | 8/2008 | Duff | |
| 2008/0199865 A1 | 8/2008 | Crossman | |
| 2008/0254476 A1 | 10/2008 | Kornman | |
| 2008/0254477 A1 | 10/2008 | Kornman | |
| 2008/0254478 A1 | 10/2008 | Kornman | |
| 2008/0311581 A1 | 12/2008 | Wyllie | |
| 2009/0023147 A1 | 1/2009 | Kornman | |
| 2009/0093396 A1 | 4/2009 | Crossman | |
| 2009/0098141 A1 | 4/2009 | Kornman et al. | |
| 2009/0163460 A1 | 6/2009 | Duff | |
| 2009/0170105 A1 | 7/2009 | Kornman | |
| 2009/0191564 A1 | 7/2009 | Francis | |
| 2010/0028893 A1 | 2/2010 | Kornman | |
| 2010/0098775 A1 | 4/2010 | Bukowski | |
| 2010/0098809 A1 | 4/2010 | Bender | |
| 2010/0105038 A1 | 4/2010 | Draper | |
| 2010/0112570 A1 | 5/2010 | Aziz | |
| 2010/0129798 A1 | 5/2010 | Abramson | |
| 2010/0136561 A1 | 6/2010 | Draper | |
| 2010/0255475 A1 | 10/2010 | Kornman | |
| 2010/0279280 A1 | 11/2010 | Wyllie | |
| 2011/0008906 A1 | 1/2011 | Aziz | |
| 2012/0208187 A1 | 8/2012 | Kornman | |
| 2013/0011841 A1 | 1/2013 | Aziz | |
| 2013/0337448 A1 | 12/2013 | Kornman et al. | |
| 2014/0356356 A1 | 12/2014 | Thuren et al. | |
| 2018/0195121 A1 | 7/2018 | Kornman et al. | |
| 2018/0195122 A1 | 7/2018 | Kornman et al. | |
| 2019/0360048 A1 | 11/2019 | Kornman et al. | |

FOREIGN PATENT DOCUMENTS

| | | |
|---|---|---|
| WO | WO 93/22456 | 11/1993 |
| WO | WO 94/16101 | 7/1994 |
| WO | WO 97/31256 | 8/1997 |
| WO | WO 00/56927 | 9/2000 |
| WO | WO 2010/048378 A2 | 4/2010 |
| WO | WO 2012/079010 A2 | 6/2012 |
| WO | WO 2013/173789 A2 | 11/2013 |
| WO | WO 2014/179625 A1 | 11/2014 |
| WO | WO 2017/123696 A1 | 7/2017 |

OTHER PUBLICATIONS

Berger, P. et al., "C-reactive protein levels are influenced by common IL-1 gene variations," Cytokine 17:171-174 (2002).

Bioque, G. et al., "Allelic polymorphism in IL-1β and IL-1 receptor antagonist (IL-1Ra) genes in inflammatory bowel disease," Clin Exp Immunol 102:379-383 (1995).

Blakemore, A. I. et al., "Interleukin-1 receptor antagonist gene polymorphism as a disease severity factor in systemic lupus erythematosus," Arthritis Rheum 37:1380-1385 (1994).

Blakemore, A. I. et al., "Interleukin-1 receptor antagonist allele (IL1RN*2) associated with nephropathy in diabetes mellitus," Hum Genet 97:369-374 (1996).

Boyle, J. P. et al., "Projection of diabetes burden through 2050: impact of changing demography and disease prevalence in the U.S.," Diabetes Care, 24(11), pp. 1936-1940 (2001).

Camp, N. J. et al., "Evidence of a pharmacogenomic response to interleukin-I receptor antagonist in rheumatoid arthritis," Genes Immun 6:467-471 (2005).

Carter, M. J. et al., "Functional correlates of the interleukin-1 receptor antagonist gene polymorphism in the colonic mucosa in ulcerative colitis," Genes Immun 5:8-15 (2004).

Carter, K. W. et al., "Association of Interleukin-1 gene polymorphisms with central obesity and metabolic syndrome in a coronary heart disease population," Hum Genet, vol. 124, No. 3, pp. 199-206 (2008).

Chen, H. et al., "Single nucleotide polymorphisms in the human interleukin-1B gene affect transcription according to haplotype context," Hum Mol Genet 15:519-529 (2006).

Chen, X. et al., "Association of six CpG-SNPs in the inflammation-related genes with coronary heart disease," Human Genomics, 2016, vol. 10, No. S2, doi: 10.1186/s40246-016-0067-1, 7 pages.

Choudhury, R. P. et al., "Arterial Effects of Canakinumab in Patients With Atherosclerosis and Type 2 Diabetes or glucose Intolerance," Journal of the American College of Cardiology 68(16):1769-80 (2016).

Clay, F. E. et al., "Interleukin 1 receptor antagonist gene polymorphism association with lichen sclerosis," Hum Genet 94:407-410 (1994).

Clay, F. E. et al., "Novel interleukin-1 receptor antagonist exon polymorphisms and their use in allele-specific mRNA assessment," Hum Genet 97:723-726 (1996).

Cominelli, F. & Pizarro, T. T., "Interleukin-1 and interleukin-1 receptor antagonist in inflammatory bowel disease," Aliment Pharmacol Ther 10, Suppl 2:49-53; discussion 54 (1996).

Cork, M. J. et al., "Psoriasis and interleukin-1. A translation," J R Coll Physicians Lond 27:366 (1993).

Cury, R. C. et al., "Acute chest pain imaging in the emergency department with cardiac computed tomography angiography," J. Nucl. Cardiol. 15(4):564-575 (2008).

Dennis, R. A. et al., "Interleukin-1 polymorphisms are associated with the inflammatory response in human muscle to acute resistance exercise," J Physiol 560:617-626 (2004).

Di Giovine, F. S. et al., "Single base polymorphism at—511 in the human interleukin-1 beta gene (IL1 beta)," Hum Mol Genet 1:450 (1992).

Duff, G. W., "Genetic variation in cytokines and relevance to inflammation and disease," In: Balkwill F, ed. The Cytokine Network Frontiers in Molecular Biology, vol. 25. Oxford: Oxford University Press, 2000:152-173.

Flegal, K. M. et al., "Prevalence and trends in obesity among US adults, 1999-2000", JAMA, vol. 288, No. 14, pp. 1723-1727 (2002).

Francis, S. E. et al., "Interleukin-1 receptor antagonist gene polymorphism and coronary artery disease," Circulation 99:861-866 (1999).

Genevay, S. et al., "Association of interleukin-4 and interleukin-1B gene variants with Larsen score progression in rheumatoid arthritis," Arthritis Rheum 47:303-309 (2002).

Giannobile, W. V. et al., "Patient Stratification for Preventive Care in Dentistry," Journal of Dental Research 92(8):694-701 (2013).

Grutters, J. C. et al., "Analysis of IL6 and IL1A gene polymorphisms in UK and Dutch patients with sarcoidosis," Sarcoidosis Vasc Diffuse Lung Dis 20:20-27 (2003).

Harrison, P. et al., "Interleukin-1 promoter region polymorphism role in rheumatoid arthritis: a meta-analysis of IL-1B-511A/G variant reveals association with rheumatoid arthritis," Rheumatology 47(12):1768-1770 (2008).

(56) References Cited

OTHER PUBLICATIONS

Heresbach, D. et al., "Significance of interleukin-1beta and interleukin-1 receptor antagonist genetic polymorphism in inflammatory bowel diseases," Am J Gastroenterol 92:1164-1169 (1997).
Hutyrova, B. et al., "Interleukin-1 gene cluster polymorphisms in sarcoidosis and idiopathic pulmonary fibrosis," Am J Respir Crit Care Med 165:148-151 (2002).
Guidance for Industry, E15 Definitions for Genomic Biomarkers, Pharmacogenomics, Pharmacogenetics, Genomic Data and Sample Coding Categories, Food & Drug Administration, Apr. 2008, 10 pages; fda.gov/Drugs/DevelopmentApprovalProcess/FromsSubmissionRequirement/ElectronicSubmissions/DataStandardsManualmonographs/ucm071667.htm.
Iacoviello, L. et al., "Polymorphisms of the interleukin-1beta gene affect the risk of myocardial infarction and ischemic stroke at young age and the response of mononuclear cells to stimulation in vitro," Arterioscler Thromb Vasc Biol 25:222-227 (2005).
Ingkanisorn, W. P. et al., "Prognosis of Negative Adenosine Stress Magnetic Resonance in Patients Presenting to an Emergency Department With Chest Pain," J. Am. Coll. Cardiol. 47(7):1427-1432 (2006).
Joo, C.-K. et al., "A Genetic Association of Proinflammatory Cytokine Genes in Korean Dry Eye Patients," ARVO Annual Meeting Abstract Search and Program Planner, vol. 52, Apr. 2011, & Annual Meeting of the Association for Research in Vision and Ophthalmology (ARVO), 2 pages.
Jouvenne, P. et al., "Possible genetic association between interleukin-1alpha gene polymorphism and the severity of chronic polyarthritis," Eur Cytokine Netw 10:33-36 (1999).
Kapelski, P. et al., "Association study of functional polymorphisms in interleukins and interleukin receptors genes: IL1A, IL1B, IL1RN, IL6, IL6R, IL10, IL10RA and TGFB1 in schizophrenia in Polish population," Schizophrenia Research, vol. 169, No. 1-3, pp. 1-9 (2015).
Kastrati, A. et al., "Protective role against restenosis from an interleukin-1 receptor antagonist gene polymorphism in patients treated with coronary stenting," J Am Coll Cardiol 36:2168-2173 (2000).
Kornman, K. S. et al., "The interleukin-1 genotype as a severity factor in adult periodontal disease," Journal of clinical periodontology 24:72-77 (1997).
Landegren, U. et al., "A Ligase-Mediated Gene Detection Technique," Science 241:1077-1080 (1988).
Latella, M. C. et al., "Interleukin 1 Gene Cluster, Myocardial Infarction at Young Age and Inflammatory response of Human Mononuclear Cells," Immunological Investigations 38:203-219 (2009).
Lavigne, P. M. & Karas, R. H. et al., "The Current State of Niacin in Cardiovascular Disease Prevention," Journal of the American College of Cardiology, vol. 61, pp. 440-446 (2013).
Libby, P., "Current concepts of the pathogenesis of the acute coronary syndromes," Circulation 104:365-372 (2001).
Libby, P., "History of Discovery: Inflammation in Atherosclerosis," Arterioscler Thromb Vasc Biol. 32(9):2045-2015 (2012).
Mansfield, J. et al., "Novel genetic association between ulcerative colitis and the anti-inflammatory cytokine interleukin-1 receptor antagonist," Gastroenterology 106:637-642 (1994).
Marcucci, R. et al., "Cardiovascular Death and Nonfatal Myocardial Infarction in Acute Coronary Syndrome Patients Receiving Coronary Stenting Are Predicted by Residual Platelet Reactivity to ADP Detected by a Point-of-Care Assay," Circulation 119:237-242 (2009).
Martin-Ventura, J. L. et al., "Biomarkers in Cardiovascular Medicine," Rev. Esp. Cardiol 62(6):677-688 (2009). (English Abstract included).
McDowell, T. L. et al., "A genetic association between juvenile rheumatoid arthritis and a novel interleukin-1 alpha polymorphism," Arthritis Rheum 38:221-228 (1995).
Na, K.-S. et al., "Proinflammatory gene polymorphisms are potentially associated with Korean non-Sjogren dry eye patients," Molecular Vision 17:2818-2823 (2011).
Nasibullin, T. R. et al., "Combinations of cytokine gene network polymorphic markers as potential predictors of myocardial infarction," Russian Journal of Genetics, vol. 50, No. 9, pp. 987-993 (2014).
Nemetez, A. et al., "IL1B gene polymorphisms influence the course and severity of inflammatory bowel disease," Immunogenetics 49:527-531 (1999).
Nicklin, M. J. H. et al., "A Sequence-Based Map of the Nine Genes of the Human Interleukin-1 Cluster," Genomics 79:718-725 (2002).
Ray, K. K. et al., "Genetic variation at the interleukin-1 locus is a determinant of changes in soluble endothelial factors in patients with acute coronary syndromes," Clinical Science 103:303-310 (2002).
Ray K. K., "Interleukin-1 Revisited: Further Insights Into Its Role in Atherosclerosis and as a Potential Therapeutic Target for Treatment," Journal of the American College of Cardiology 63(17):1735-1738 (2014).
Read, R. C. et al., "An interleukin-1 genotype is associated with fatal outcome of meningococcal disease," J Infect Dis 182:1557-1560 (2000).
Ridker, P. M. et al., "Rosuvastatin to prevent vascular events in men and women with elevated C-reactive protein," N Engl J Med., 359, pp. 2195-2207 (2008).
Ridker, P. M., "Targeting inflammatory pathways for the treatment of cardiovascular disease," European Heart Journal 35:540-543 (2014).
Riha, R. L. et al., "Cytokine gene polymorphisms in idiopathic pulmonary fibrosis," Intern Med J 34:126-129 (2004).
Rogus, J., et al., "IL1B Gene Promoter Haplotype Pairs Predict Clinical Levels of Interleukin-1β and C-reactive Protein," Human Genetics 123(4):387-398 (2008).
Ross, R., "Atherosclerosis—An inflammatory disease," N Engl J Med 340:115-126 (1999).
Ruperto, N. et al., "Two randomized trials of canakinumab in systemic juvenile idiopathic arthritis," The New England Journal of Medicine 367:2396-2406 (2012).
Schillinger, M. et al., "Acute chest pain—identification of patients at low risk for coronary events. The impact of symptoms, medical history and risk factors," Wiener Klin. Wochenschr. 116(3):83-89 (2004).
Selvaraj, C. L. et al., "Point-of-Care Determination of Baseline Platelet Function as a Predictor of Clinical Outcomes in Patients who Present to the Emergency Department with Chest Pain," J. Throm. Thrombolysis 18(2):109-115, 2004.
Sharma, R. K. et al., "Coronary computed tomographic angiography (CCTA) in community hospitals: 'current and emerging role,'" Vasc. Health Risk Manag. 6:307-316 (2010).
Srivatsan, A. et al., "High-Precision, Whole-Genome Sequencing of Laboratory Strains Facilitates Genetic Studies," PLoS Genet 4: e1000139 (2008), 14 pages; doi:10.1371/journal.pgen.1000139.
Tadros, "Clinical Predictors of 30-day Cardiac Events in Patients with Acute Coronary Syndrome at a Community Hospital", South Med. J. 96, p. 1113-1120, 2003.
Tarlow, J. K. et al., "Severity of alopecia areata is associated with a polymorphism in the interleukin-1 receptor antagonist gene," J Invest Dermatol 103:387-390 (1994).
Tarlow, J. K. et al., "Association between interleukin-1 receptor antagonist (IL-1ra) gene polymorphism and early and late-onset psoriasis," Br J Dermatol 136:147-148 (1997).
Thompson, P. L. & Nidorf, M. S., "Anti-inflammatory therapy with canakinumab for atherosclerotic disease: lessons from the CANTOS trial," Journal of Thoracic Disease 10(2):695-698 (2018).
Timms, A. E. et al., "The interleukin 1 gene cluster contains a major susceptibility locus for ankylosing spondylitis," American Journal of Human Genetics 75:587-595 (2004).
Tountas, N. A. et al., "Functional and ethnic association of allele 2 of the interleukin-1 receptor antagonist gene in ulcerative colitis," Gastroenterology 117:806-813 (1999).
Tsimikas, S. et al., "Oxidized Phospholipids, Lp(a) Lipoprotein, and Coronary Artery Disease," New England Journal of Medicine 353:46-57 (2005).
Tsimikas, S. et al., "Pro-Inflammatory Interleukin-1 Genotypes Potentiate the risk of Coronary Artery Disease and Cardiovascular

(56) References Cited

OTHER PUBLICATIONS

Events Mediated by Oxidized Phospholipids and Lipoprotein(a)" J. Am. College of Cardiology 63(17):1724-1734 (2014).
Tsimikas, S. et al., "The Influence of Oxidized Phospholipids and Lp(a) Lipoprotein on Coronary Artery Disease is Conditional upon Genotype at the Interleukin-1 Region," American College of Cardiology Annual Meeting, New Orleans 2007, 1 page.
Tunstall-Pedoe, H. et al., "Estimation of contribution of changes in coronary care to improving survival, event rates, and coronary heart disease mortality across the WHO MONICA Project populations", The Lancet, 355(9205), pp. 688-700 (2000).
Vargas-Alarcón, G. et al., "The interleukin-1β-511 T>C (rs16944) gene polymorphism is associated with risk of developing silent myocardial ischemia in diabetic patients," Immunology Letters, vol. 168, No. 1, pp. 7-12 (2015).
Viney, N. J. et al.., "Antisense oligonucleotides targeting apolipoprotein(a) in people with raised lipoprotein(a): two randomized, double-blind, placebo controlled, dose-ranging trials," The Lancet 388:2239-2253 (2016).
Whyte, M. et al., "Increased risk of fibrosing alveolitis associated with interleukin-1 receptor antagonist and tumor necrosis factor-alpha gene polymorphisms," Am J Respir Crit Care Med 162:755-758 (2000).
Wise, C. A. et al., "A standard protocol for single nucleotide primer extension in the human genome using matrix-assisted laser desorption/ionization time-of-flight mass spectrometry," Rapid Comm. Mass Spect. 17(11):1195-202 (2003).
Wong, M. D. et al., "Contribution of major diseases to disparities in mortality," N Engl J Med 347(20):1585-92 (2002).
Yang, H. T. et al., "Association of interleukin gene polymorphisms with the risk of coronary artery disease," Genetics and Molecular Research, vol. 14, No. 4, pp. 12489-12496 (2015).
Yucesoy, B. et al., "Polymorphisms of the IL-1 gene complex in coal miners with silicosis," Am J Ind Med 39:286-291 (2001).
Yusuf, S. et al., "Global burden of cardiovascular diseases: part I: general considerations, the epidemiologic transition, risk factors, and impact of urbanization," Circulation 104(22):2746-53 (2001).
Yusuf, S., et al., "Global burden of cardiovascular diseases: Part II: variations in cardiovascular disease by specific ethnic groups and geographic regions and prevention strategies," Circulation 104(23):2855-64 (2001).
Yusuf, S. et al., "Effect of potentially modifiable risk factors associated with myocardial infarction in 52 countries (the Interheart study): case-control study," Lancet 364:937-52 (2004).
Zhang, G. et al., "A negative regulatory region containing a glucocorticosteroid response element (nGRE) in the human interleukin-1β gene," DNA Cell Biol 16:145-152 (1997).
www.fda.gov/downloads/RegulatoryInformation/Guidances/ucm129296.pdf.
Araya et al., Trends Biotechnology doi10.1016.j.tibtech.2011.04.003 (2011).
Chen et al., "Single nucleotide polymorphism genotyping: biochemistry, protocol, cost and throughput," Pharmacogenomics J 3 (2):77-96 (2003).
Cohen et al., Adv Chromatogr 36:127-162 (1996).
Corey, "Peptide nucleic acids: expanding the scope of nucleic acid recognition," Trends Biotechnol 15 (6):224-9 (Jun. 1997).
Gibbs, Nucleic Acid Res 17:2427-2448 (1989).
Goodman & Gilman's The Pharmacological Basis of Therapeutics, Twelfth Edition (2011), Appendix II, pp. 1891-1991, and the Physicians' Desk Reference 70$^{th}$ Edition, 2016.
Griffin et al, Appl Biochem Biotechnol 38:147-159 (1993).
Guatelli et al., Proc Natl Acad Sci USA 87:1874 (1990).
Hyrup et al., "Peptide nucleic acids (PNA): synthesis, properties and potential applications," Bioorg Med Chem 4 (1):5-23 (Jan. 1996).
Kwok et al., "Detection of single nucleotide polymorphisms," Curr Issues Mol Biol 5 (2):43-60 (Apr. 2003).
Kwok, "Methods for genotyping single nucleotide polymorphisms," Annu Rev Genom Hum Genet 2:235-58 (2001).
Li et al., Nature 463: 311-317 (2010).
Livak et al., PCR Method Appl 4:357-362 (1995).
Lo et al., Clin Chem 55: 607-608 (2009).
Mamellos, "High-throughput SNP analysis for genetic association studies," Curr Opin Drug Disc Devel 6 (3):317-21 (May 2003).
McEllistrem, Future Microbiol 4: 857-865 (2009).
Myers et al., Nature 313:495 (1985).
Nazarenko et al., Nuc' Acids Res 25:2516-2521 (1997).
PCR Technology: Principles and Applications for DNA Amplification, ed. H. A. Erlich, Freeman Press, NY, N.Y. (1992).
Pelak et al., PLoS Genet 6: e1001111 (2010).
Ram et al., Syst Biol Reprod Med (57(3):117-118 (2011).
Rasmussen et al., Nature 463:757-762 (2010).
Robinson, Genome Biol 11:144 (2010).
Saiki et al., Nature 324:163-166 (1986).
Shi, "Technologies for individual genotyping: detection of genetic polymorphisms in drug targets and disease genes," Am J Pharmacogenomics 2 (3):197-205 (2002).
Tyagi et al., Nature Biotechnology 14:303-308 (1996).
U.S. Appl. No. 60/427,818.
U.S. Appl. No. 60/445,494.
U.S. Appl. No. 60/445,636.
Web (www)fda.gov/Drugs/DevelopmentApprovalProcess/FormsSubmissionRequirements/ElectronicSubmissions/DataStandardsManualmonographs/ucm071667.htm.
Wise et al., "A standard protocol for single nucleotide primer extension in the human genome using matrix-assisted laser desorption/ionization time-of-flight mass spectrometry," Rapid Comm. Mass Spect. 17 (11):1195-202 (2003).
Wu and Wallace, Genomics 4:560 (1989); Landegren et al., Science 241:1077 (1988).
Ridker, P. M., "How Common Is Residual Inflammatory Risk?" Circ Res., 120:617-619 (2017).
Ilaris® (canakinumab) product label, downloaded from http://www.ilaris.com/...IVU1mGCh2BdwBbEAAYASAAEgKplvD_BwE&usertrack.filter_applied=filter_applied=true&Novald=3831502932843554108, 2 pages.
López-Castejón, G. & Pelegrín, P., "Current status of inflammasome blockers as antinflammatory drugs," Expert Opinion on Investigational Drugs, 21(7):995-1007 (2012).

METHODS FOR PREDICTING RESPONSE TO TREATMENT

RELATED APPLICATIONS

This application claims priority to and benefit of U.S. Provisional Application No. 62/277,760, filed Jan. 12, 2016, the contents of which are incorporated herein by reference in their entirety.

FIELD OF THE INVENTION

This invention relates to a method and kits for detecting a predisposition to, determining risk of, and guiding therapy for inflammation-related disorders.

BACKGROUND OF THE INVENTION

Inflammation is a critical protective mechanism of the innate immune system that is activated in response to many external and internal challenges. It involves release of pre-formed mediators such as complement and histamines and activation of early response genes, of which interleukin-1 (IL-1) and tumor necrosis factor alpha (TNFα) genes are among the best documented. The IL-1 gene family includes 11 different genes, of which the genes for the agonists IL-1α (IL1A) and IL-1β (IL1B), and the natural antagonist IL-1 receptor antagonist (IL1RN) are the best characterized. These three IL-1 components have substantial biological and clinical effects relative to multiple conditions and diseases. IL-1β and TNFα stimulate each other's production and reinforce each other's biological activities. IL-1β rapidly activates multiple inflammatory cascades. One of the most prominent early systemic responses to an inflammatory insult involves activation of acute phase proteins in the liver, which leads to release of high quantities of these proteins into the bloodstream. This release initially amplifies and then dampens the innate immune response.

Inflammation is a major control point for many chronic diseases. In spite of the complexity of the innate immune response, there is hierarchy in the system as evidenced by successful development of clinically valuable drugs that target early leverage points in the inflammatory system, most prominently IL-1 and TNFα. The importance of chronic over-expression of innate immunity to overall health is evident in the expanding indications for drugs that control IL-1 and TNFα. There are many currently-ongoing clinical programs that are evaluating drugs directly targeting IL-1 biologic activity for treating diseases ranging from type II diabetes mellitus, to cardiovascular events, and to moderate or severe allergic conjunctivitis. Chronic inflammatory diseases, usually being life-long, account for approximately 83% of current healthcare costs in the U.S. Finally, chronic inflammation is known to be a risk factor that significantly affects healthful longevity.

Certain anti-inflammatory drugs target early leverage points in the inflammatory cascade and, in particular, points in the cascade relating to IL-1 and TNFα production or IL-1 TNFα biologic activity. Some individuals are known to be "high producers" of IL-1 and others are "low producers" of IL-1. There exists a need for methods and kits to identify whether an individual who has an inflammation-related disorder is a "high" or "low" producer of IL-1 such that s/he can be provided with an appropriate anti-inflammatory drug at an appropriate dose

SUMMARY OF THE INVENTION

The present invention provides stratification methods and kits to identify whether an individual having an inflammation-related disorder has genotype-specific differential expression of IL-1, i.e., is a "high" or "low" producer of IL-1, such that s/he can be provided an appropriate anti-inflammatory drug at an appropriate dose (e.g., the dose of a single treatment and/or a daily dose comprising one or more single treatments) to reduce IL-1 directed inflammation. The stratification of high or low IL-1 producers to guide assignment of different drug doses may also reduce drug toxicity and adverse events in an individual who, without stratification, may be prescribed a higher dose than needed to manage the primary indication. The use of IL-1 stratification of drug dosing would allow a better clinical benefit-risk appraisal in an individual patient.

An aspect of the present invention relates to a method for stratifying a human population, e.g., for a clinical trial, comprising steps of (a) selecting a plurality of human subjects in the population; (b) obtaining an isolated nucleic acid from a biological sample from each of the plurality of human subjects; (c) detecting the single nucleotide polymorphism (SNP) alleles in each isolated nucleic acid for each of the IL1B (−511) rs16944 C>T polymorphic locus, the IL1B (−1464) rs1143623 G>C polymorphic locus, and the IL1B (−3737) rs4848306 C>T polymorphic locus for each human subject; (d) determining each human subject's Composite IL-1 Genetic Pattern based on the detecting in step (c) and the information disclosed in Table 1; and (e) assigning each human subject into a study group based on the human subject's Composite IL-1 Genetic Pattern. The method may further comprise detecting the SNP alleles in the isolated nucleic acid for each of the IL1A (+4845) rs17561G>T polymorphic locus and the IL1B (+3954) rs1143634 C>T polymorphic locus for each human subject. Subjects with Composite IL-1 Genetic Pattern 1 and subjects with Composite IL-1 Genetic Pattern 3 may be assigned to separate study groups. Subjects with Composite IL-1 Genetic Pattern 1 and subjects with Composite IL-1 Genetic Pattern 2 may be assigned to separate study groups. Subjects with Composite IL-1 Genetic Pattern 2 and subjects with Composite IL-1 Genetic Pattern 3 may be assigned to separate study groups. Subjects with Composite IL-1 Genetic Pattern 1 and subjects with Composite IL-1 Genetic Pattern 2 may be assigned to the same study group. Subjects with Composite IL-1 Genetic Pattern 1, with Composite IL-1 Genetic Pattern 2, and subjects with Composite IL-1 Genetic Pattern 3 may be assigned to separate study groups. A human subject may have, is suspected of having, or at risk for having an IL 1β-related disorder or cardiovascular disease.

Another aspect of the present invention relates to a method for stratifying a human population for a clinical trial relating to the safety and/or efficacy of Isunakinra, comprising steps of: (a) selecting a plurality of human subjects in the population; (b) obtaining an isolated nucleic acid from a biological sample from each of the plurality of human subjects; (c) detecting the single nucleotide polymorphism (SNP) alleles in each isolated nucleic acid for each of the IL1B (−511) rs16944 C>T polymorphic locus, the IL1B (−1464) rs1143623 G>C polymorphic locus, and the IL1B (−3737) rs4848306 C>T polymorphic locus for each human subject; (d) determining each human subject's Composite IL-1 Genetic Pattern based on the detecting in step (c) and the information disclosed in Table 1; and (e) assigning each human subject into a study group based on the human subject's Composite IL-1 Genetic Pattern. The method may further comprise detecting the SNP alleles in the isolated nucleic acid for each of the IL1A (+4845) rs17561G>T polymorphic locus and the IL1B (+3954) rs1143634 C>T polymorphic locus for each human subject. Subjects with Composite IL-1 Genetic Pattern 1 and subjects with Composite IL-1 Genetic Pattern 3 may be assigned to separate study groups. Subjects with Composite IL-1 Genetic Pattern 1 and subjects with Composite IL-1 Genetic Pattern 2 may be assigned to separate study groups. Subjects with Composite IL-1 Genetic Pattern 2 and subjects with Composite IL-1 Genetic Pattern 3 may be assigned to separate study groups. Subjects with Composite IL-1 Genetic Pattern 1 and subjects with Composite IL-1 Genetic Pattern 2 may be assigned to the same study group. Subjects with Composite IL-1 Genetic Pattern 1, with Composite IL-1 Genetic Pattern 2, and subjects with Composite IL-1 Genetic Pattern 3 may be assigned to separate study groups. A human subject may have, is suspected of having, or at risk for having an IL 1β-related disorder or cardiovascular disease. The human subject may have, is suspected of having, or at risk for having allergic conjunctivitis (AC) and/or dry eye disease.

Yet another aspect of the present invention relates to a method comprising steps of: (a) selecting a human subject with a diagnosis of, suspected of having, or at risk for an IL 1β-related disorder; (b) obtaining an isolated nucleic acid from a biological sample from the human subject; (c) detecting the single nucleotide polymorphism (SNP) alleles in the isolated nucleic acid for each of the IL1B (−511) rs16944 C>T polymorphic locus, the IL1B (−1464) rs1143623 G>C polymorphic locus, and the IL1B (−3737) rs4848306 C>T polymorphic locus; (d) determining each human subject's Composite IL-1 Genetic Pattern based on the detecting in step (c) and the information disclosed in Table 1; and (e) providing a recommendation for a therapeutic regimen based upon the human subject's Composite IL 1 Genetic Pattern. The method may further comprise detecting the SNP alleles in the isolated nucleic acid for each of the IL1A (+4845) rs17561G>T polymorphic locus and the IL1B (+3954) rs1143634 C>T polymorphic locus. Subjects with Composite IL-1 Genetic Pattern 1 and subjects with Composite IL-1 Genetic Pattern 3 may be provided different therapeutic regimen recommendations. Subjects with Composite IL-1 Genetic Pattern 1 and subjects with Composite IL-1 Genetic Pattern 2 may be provided different therapeutic regimen recommendations. Subjects with Composite IL-1 Genetic Pattern 1 and subjects with Composite IL-1 Genetic Pattern 2 may be provided the same therapeutic regimen recommendation. Subjects with Composite IL-1 Genetic Pattern 2 and subjects with Composite IL-1 Genetic Pattern 3 may be provided the same therapeutic regimen recommendation. Subjects with Composite IL-1 Genetic Pattern 1, subjects with Composite IL-1 Genetic Pattern 2, and subjects with Composite IL-1 Genetic Pattern 3 may be provided different therapeutic regimen recommendations. The human subject may have, suspected of having, or at risk for having an IL 1β-related disorder or cardiovascular disease. In embodiments, the human subject with Composite IL-1 Genetic Pattern 1 is provided a recommendation for (i) an aggressive therapeutic regimen comprising a drug that inhibits IL-1β activity, (ii) a mild therapeutic regimen comprising a drug that inhibits IL-1β activity, or (iii) a therapeutic regimen not comprising a drug that inhibits IL-1β activity. In embodiments, the human subject with Composite IL-1 Genetic Pattern 2 is provided a recommendation for (i) an aggressive therapeutic regimen comprising a drug that inhibits IL-1β activity, (ii) a mild therapeutic regimen comprising a drug that inhibits IL-1β activity, or (iii) a therapeutic regimen not comprising a drug that inhibits IL-1β activity. In embodiments, the human subject with Composite IL-1 Genetic Pattern 3 is provided a recommendation for (i) an aggressive therapeutic regimen comprising a drug that inhibits IL-1β activity, (ii) a mild therapeutic regimen comprising a drug that inhibits IL-1β activity, or (iii) a therapeutic regimen not comprising a drug that inhibits IL-1β activity. In any of the above embodiments of this aspect, the therapeutic regimen comprises a drug selected from Table 2 and/or an alternate drug having a mode of action similar to or identical to a drug from Table 2.

An aspect of the present invention relates to a method comprising steps of: (a) selecting a human subject with a diagnosis of, suspected of having, or at risk for allergic conjunctivitis (AC) and/or dry eye disease; (b) obtaining an isolated nucleic acid from a biological sample from the human subject; (c) detecting the single nucleotide polymorphism (SNP) alleles in the isolated nucleic acid for each of the IL1B (−511) rs16944 C>T polymorphic locus, the IL1B (−1464) rs1143623 G>C polymorphic locus, and the IL1B (−3737) rs4848306 C>T polymorphic locus; (d) determining each human subject's Composite IL-1 Genetic Pattern based on the detecting in step (c) and the information disclosed in Table 1; and (e) providing a recommendation for a therapeutic regimen comprising Isunakinra based upon the human subject's Composite IL 1 Genetic Pattern. The method may further comprise detecting the SNP alleles in the isolated nucleic acid for each of the IL1A (+4845) rs17561G>T polymorphic locus and the IL1B (+3954) rs1143634 C>T polymorphic locus. Subjects with Composite IL-1 Genetic Pattern 1 or 2 and subjects with Composite IL-1 Genetic Pattern 3 may be provided different therapeutic regimen recommendations. Subjects with Composite IL-1 Genetic Pattern 1 and subjects with Composite IL-1 Genetic Pattern 2 may be provided the same therapeutic regimen recommendation. The human subject with Composite IL-1 Genetic Pattern 1 or 2 may be provided a recommendation for (i) an aggressive therapeutic regimen comprising Isunakinra or (ii) a mild therapeutic regimen comprising Isunakinra. The human subject with Composite IL-1 Genetic Pattern 3 may be provided a recommendation for a therapeutic regimen not comprising Isunakinra. An aggressive therapeutic regimen comprises a higher dose of Isunakinra than a mild therapeutic regimen comprising Isunakinra. When provided, the recommended therapeutic regimen comprises Isunakinra is formulated at between about 1 mg/ml and about 50 mg/ml, e.g., about 5 mg/ml or about 20 mg/ml. The recommended therapeutic regimen which comprises providing Isunakinra is between about once per day and about five times per day, e.g., about three times per day.

Another aspect of the present invention relates to a method comprising steps of: (a) selecting a human subject with a diagnosis of, suspected of having, or at risk for an IL 1β-related disorder; (b) obtaining an isolated nucleic acid from a biological sample from the human subject; (c) detecting the single nucleotide polymorphism (SNP) alleles in the isolated nucleic acid for each of the IL1B (−511) rs16944 C>T polymorphic locus, the IL1B (−1464) rs1143623 G>C polymorphic locus, and the IL1B (−3737) rs4848306 C>T polymorphic locus; (d) determining each human subject's Composite IL-1 Genetic Pattern based on the detecting in step (c) and the information disclosed in Table 1; and (e) providing a therapeutic regimen based the human subject's Composite IL 1 Genetic Pattern. The method may further comprise detecting the SNP alleles in the isolated nucleic acid for each of the IL1A (+4845) rs17561G>T polymorphic locus and the IL1B (+3954) rs1143634 C>T polymorphic locus. Subjects with Composite IL-1 Genetic Pattern 1 and subjects with Composite IL-1 Genetic Pattern 3 may be provided different therapeutic regimens. Subjects with Composite IL-1 Genetic Pattern 2 may be provided different therapeutic regimens. Subjects with Composite IL-1 Genetic Pattern 1 and subjects with Composite IL-1 Genetic Pattern 2 may be provided the same therapeutic regimen. Subjects with Composite IL-1 Genetic Pattern 2 and subjects with Composite IL-1 Genetic Pattern 3 may be provided the same therapeutic regimen. Subjects with Composite IL-1 Genetic Pattern 1, subjects with Composite IL-1 Genetic Pattern 2, and subjects with Composite IL-1 Genetic Pattern 3 may be provided different therapeutic regimens. The human subject may have, is suspected of having, or at risk for having an IL 1β-related disorder or cardiovascular disease. In embodiments, the human subject with Composite IL-1 Genetic Pattern 1 is provided (i) an aggressive therapeutic regimen comprising a drug that inhibits IL-1β activity, (ii) a mild therapeutic regimen comprising a drug that inhibits IL-1β activity, or (iii) a therapeutic regimen not comprising a drug that inhibits IL-1β activity. In embodiments, the human subject with Composite IL-1 Genetic Pattern 2 is provided (i) an aggressive therapeutic regimen comprising a drug that inhibits IL-1β activity, (ii) a mild therapeutic regimen comprising a drug that inhibits IL-1β activity, or (iii) a therapeutic regimen not comprising a drug that inhibits IL-1β activity. In embodiments, the human subject with Composite IL-1 Genetic Pattern 3 is provided (i) an aggressive therapeutic regimen comprising a drug that inhibits IL-1β activity, (ii) a mild therapeutic regimen comprising a drug that inhibits IL-1β activity, or (iii) a therapeutic regimen not comprising a drug that inhibits IL-1β activity. In any of the above embodiments of this aspect, the therapeutic regimen comprises a drug selected from Table 2, and/or an alternate drug having a mode of action similar to or identical to a drug from Table 2.

Yet another aspect of the present invention relates to a method comprising steps of: (a) selecting a human subject with a diagnosis of, suspected of having, or at risk for allergic conjunctivitis (AC) and/or dry eye disease; (b) obtaining an isolated nucleic acid from a biological sample from the human subject; (c) detecting the single nucleotide polymorphism (SNP) alleles in the isolated nucleic acid for each of the IL1B (−511) rs16944 C>T polymorphic locus, the IL1B (−1464) rs1143623 G>C polymorphic locus, and the IL1B (−3737) rs4848306 C>T polymorphic locus; (d) determining each human subject's Composite IL-1 Genetic Pattern based on the detecting in step (c) and the information disclosed in Table 1; and (e) providing a therapeutic regimen based the human subject's Composite IL 1 Genetic Pattern. The method may further comprise detecting the SNP alleles in the isolated nucleic acid for each of the IL1A (+4845) rs17561G>T polymorphic locus and the IL1B (+3954) rs1143634 C>T polymorphic locus. Subjects with Composite IL-1 Genetic Pattern 1 or 2 and subjects with Composite IL-1 Genetic Pattern 3 may be provided different therapeutic regimens. Subjects with Composite IL-1 Genetic Pattern 1 and subjects with Composite IL-1 Genetic Pattern 2 may be provided the same therapeutic regimen. The human subject with Composite IL-1 Genetic Pattern 1 or 2 may be provided (i) an aggressive therapeutic regimen comprising Isunakinra or (ii) a mild therapeutic regimen comprising Isunakinra. The human subject with Composite IL-1 Genetic Pattern 3 may be provided a therapeutic regimen not comprising Isunakinra. The therapeutic regimen comprises Isunakinra is formulated at between about 1 mg/ml and about 50 mg/ml, when provided. When provided, the Isunakinra is formulated at about 5 mg/ml or about 20 mg/ml. When provided, the therapeutic regimen comprising Isunakinra is provided between about once per day and about five times per day, e.g., about three times per day.

An aspect of the present invention relates to a method for treating a human subject having or at risk for an IL 1β-related disorder comprising steps of: (a) obtaining information regarding the human subject's single nucleotide polymorphism (SNP) alleles for each of the IL1B (−511) rs16944 C>T polymorphic locus, the IL1B (−1464) rs1143623 G>C polymorphic locus, and the IL1B (−3737) rs4848306 C>T polymorphic locus; (b) determining the human subject's Composite IL-1 Genetic Pattern based on the information obtained in step (a) and the information disclosed in Table 1; and (c) providing a drug that inhibits IL 1β activity to the human subject. The method may further comprise obtaining information regarding the human subject's SNP alleles for each of the IL1A (+4845) rs17561G>T polymorphic locus and the IL1B (+3954) rs1143634 C>T polymorphic locus. In embodiments, the human subject with Composite IL-1 Genetic Pattern 1 is provided (i) an aggressive therapeutic regimen comprising the drug that inhibits IL-1β activity, (ii) a mild therapeutic regimen comprising the drug that inhibits IL-1β activity, or (iii) a therapeutic regimen not comprising the drug that inhibits IL-1β activity. In embodiments, the human subject with Composite IL-1 Genetic Pattern 2 is provided (i) an aggressive therapeutic regimen comprising the drug that inhibits IL-1β activity, (ii) a mild therapeutic regimen comprising the drug that inhibits IL-1β activity, or (iii) a therapeutic regimen not comprising the drug that inhibits IL-1β activity. In embodiments, the human subject with Composite IL-1 Genetic Pattern 3 is provided (i) an aggressive therapeutic regimen comprising the drug that inhibits IL-1β activity, (ii) a mild therapeutic regimen comprising the drug that inhibits IL-1β activity, or (iii) a therapeutic regimen not comprising the drug that inhibits IL-1β activity. An aggressive therapeutic regimen comprises a higher dose of the drug that inhibits IL-1β activity than a mild therapeutic regimen. In any of the above embodiments of this aspect, the drug is selected from Table 2 and/or an alternate drug having a mode of action similar to or identical to a drug from Table 2.

Another aspect of the present invention relates to a method for treating a human subject having or at risk for allergic conjunctivitis (AC) and/or dry eye disease comprising steps of: (a) obtaining information regarding the human subject's single nucleotide polymorphism (SNP) alleles for each of the IL1B (−511) rs16944 C>T polymorphic locus, the IL1B (−1464) rs1143623 G>C polymorphic locus, and the IL1B (−3737) rs4848306 C>T polymorphic locus; (b) determining the human subject's Composite IL-1 Genetic Pattern based on the information obtained in step (a) and the information disclosed in Table 1; and (c) providing a therapeutic regimen to the human subject thereby treating allergic AC and/or dry eye disease that is IL-1 governing. The method may further comprise obtaining information regarding the human subject's SNP alleles for each of the IL1A (+4845) rs17561G>T polymorphic locus and the IL1B (+3954) rs1143634 C>T polymorphic locus. Subjects with Composite IL-1 Genetic Pattern 1 or 2 and subjects with Composite IL-1 Genetic Pattern 3 may be provided different therapeutic regimens. Subjects with Composite IL-1 Genetic Pattern 1 and subjects with Composite IL-1 Genetic Pattern 2 may be provided the same therapeutic regimen. The human subject with Composite IL-1 Genetic Pattern 1 or 2 may be provided (i) an aggressive therapeutic regimen comprising Isunakinra or (ii) a mild therapeutic regimen comprising Isunakinra. The human subject with Composite IL-1 Genetic Pattern 3 may be provided a therapeutic regimen not comprising Isunakinra. An aggressive therapeutic regimen comprises a higher dose of Isunakinra than a mild therapeutic regimen. When provided, the therapeutic regimen comprising Isunakinra is formulated at between about 1 mg/ml and about 50 mg/ml, e.g., about 5 mg/ml or about 20 mg/ml. When provided, the therapeutic regimen comprising Isunakinra is provided between about once per day and about five times per day, e.g., about three times per day.

Yet another aspect of the present invention relates to a method for determining whether a human subject is predisposed to having an IL 1β-related disorder: (a) obtaining an isolated nucleic acid from a biological sample from the human subject; (b) detecting the single nucleotide polymorphism (SNP) alleles in the isolated nucleic acid for each of the IL1B (−511) rs16944 C>T polymorphic locus, the IL1B (−1464) rs1143623 G>C polymorphic locus, and the IL1B (−3737) rs4848306 C>T polymorphic locus; and (c) determining the human subject's Composite IL-1 Genetic Pattern based on the detecting in step (c) and the information disclosed in Table 1. The method may further comprise detecting the SNP alleles in the isolated nucleic acid for each of the IL1A (+4845) rs17561G>T polymorphic locus and the IL1B (+3954) rs1143634 C>T polymorphic locus. When the human subject has Composite IL-1 Genetic Pattern 1, the human subject is predisposed to having an IL 1β-related disorder. When the human subject has Composite IL-1 Genetic Pattern 2, the human subject is predisposed to having an IL 1β-related disorder. When the human subject has Composite IL-1 Genetic Pattern 2, the human subject is not predisposed to having an IL 1β-related disorder. When the human subject has Composite IL-1 Genetic Pattern 3, the human subject is not predisposed to having an IL 1β-related disorder. In any of the above embodiments of this aspect, the IL 1β-related disorder is allergic conjunctivitis (AC) and/or dry eye disease.

An aspect of the present invention relates to a method for determining whether a human subject having an IL 1β-related disorder would receive a therapeutic benefit from/would be responsive to a drug that inhibits IL 1β activity comprising steps of: (a) obtaining an isolated nucleic acid from a biological sample from the human subject; (b) detecting the single nucleotide polymorphism (SNP) alleles in the isolated nucleic acid for each of the IL1B (−511) rs16944 C>T polymorphic locus, the IL1B (−1464) rs1143623 G>C polymorphic locus, and the IL1B (−3737) rs4848306 C>T polymorphic locus; and (c) determining the human subject's Composite IL-1 Genetic Pattern based on the detecting in step (b) and the information disclosed in Table 1; wherein a human subject with Composite IL-1 Genetic Pattern 1 would receive a therapeutic benefit from/would be responsive to a drug that inhibits IL 1β activity and a human subject with Composite IL-1 Genetic Pattern 3 would not receive a therapeutic benefit from/would be responsive to a drug that inhibits IL 1β activity. The method further comprises detecting the SNP alleles in the isolated nucleic acid for each of the IL1A (+4845) rs17561G>T polymorphic locus and the IL1B (+3954) rs1143634 C>T polymorphic locus. A human subject with Composite IL-1 Genetic Pattern 2 would receive a therapeutic benefit from/would be responsive to a drug that inhibits IL 1β activity. A human subject with Composite IL-1 Genetic Pattern 2 would not receive a therapeutic benefit from/would be responsive to a drug that inhibits IL 1β activity. In any of the above embodiments of this aspect, the drug is selected from Table 2 and/or an alternate drug having a mode of action similar to or identical to a drug from Table 2.

Another aspect of the present invention relates to a method for determining whether a human subject having allergic conjunctivitis (AC) and/or dry eye disease would receive a therapeutic benefit from/would be responsive to Isunakinra comprising steps of: (a) obtaining an isolated nucleic acid from a biological sample from the human subject; (b) detecting the single nucleotide polymorphism (SNP) alleles in the isolated nucleic acid for each of the IL1B (−511) rs16944 C>T polymorphic locus, the IL1B (−1464) rs1143623 G>C polymorphic locus, and the IL1B (−3737) rs4848306 C>T polymorphic locus; and (c) determining the human subject's Composite IL-1 Genetic Pattern based on the detecting in step (b) and the information disclosed in Table 1; wherein a human subject with Composite IL-1 Genetic Pattern 1 or 2 would receive a therapeutic benefit from/would be responsive to Isunakinra and a human subject with Composite IL-1 Genetic Pattern 3 would not receive a therapeutic benefit from/would be responsive to Isunakinra. The method may further comprise detecting the SNP alleles in the isolated nucleic acid for each of the IL1A (+4845) rs17561G>T polymorphic locus and the IL1B (+3954) rs1143634 C>T polymorphic locus.

Yet another aspect of the present invention relates to a kit comprising: (a) reagents for detecting the single nucleotide polymorphism (SNP) alleles in the isolated nucleic acid for each of the IL1B (−511) rs16944 C>T polymorphic locus, the IL1B (−1464) rs1143623 G>C polymorphic locus, and the IL1B (−3737) rs4848306 C>T polymorphic locus; (b) instructions for determining a human subject's Composite IL-1 Genetic Pattern based on the detecting in step (a) and the information disclosed in Table 1; and (c) instructions for determining whether a subject is predisposed to having an IL 1β-related disorder/would receive a therapeutic benefit from/would be responsive to a drug that inhibits IL 1β activity based upon the human subject's Composite IL-1 Genetic Pattern. The kit may further comprise reagents for detecting the SNP alleles in the isolated nucleic acid for each of the IL1A (+4845) rs17561G>T polymorphic locus and the IL1B (+3954) rs1143634 C>T polymorphic locus. In any embodiment of this aspect, the drug is selected from Table 2 and/or an alternate drug having a mode of action similar to or identical to a drug from Table 2.

An aspect of the present invention relates to a kit comprising: (a) reagents for detecting the single nucleotide polymorphism (SNP) alleles in the isolated nucleic acid for each of the IL1B (−511) rs16944 C>T polymorphic locus, the IL1B (−1464) rs1143623 G>C polymorphic locus, and the IL1B (−3737) rs4848306 C>T polymorphic locus; (b) instructions for determining a human subject's Composite IL-1 Genetic Pattern based on the detecting in step (a) and the information disclosed in Table 1; and (c) instructions for determining whether a subject is predisposed to having an IL 1β-related disorder/would receive a therapeutic benefit from/would be responsive to Isunakinra based upon the human subject's Composite IL-1 Genetic Pattern. The kit may further comprise reagents for detecting the SNP alleles in the isolated nucleic acid for each of the IL1A (+4845) rs17561G>T polymorphic locus and the IL1B (+3954) rs1143634 C>T polymorphic locus. In any embodiment of this aspect, the IL 1β-related disorder is allergic conjunctivitis (AC) and/or dry eye disease.

Another aspect of the present invention relates to a method for stratifying a human population after completion of a clinical trial comprising steps of: (a) obtaining an isolated nucleic acid from a biological sample from a plurality of human subjects who have undergone a clinical trial; (b) detecting the single nucleotide polymorphism (SNP) alleles in each isolated nucleic acid for each of the IL1B (−511) rs16944 C>T polymorphic locus, the IL1B (−1464) rs1143623 G>C polymorphic locus, and the IL1B (−3737) rs4848306 C>T polymorphic locus for each human subject; (c) determining each human subject's Composite IL-1 Genetic Pattern based on the detecting in step (b) and the information disclosed in Table 1; and (d) reassessing data from the completed clinical trial for each human subject in view of each human subject's Composite IL-1 Genetic Pattern. The method may further comprise detecting the SNP alleles in each isolated nucleic acid for each of the IL1A (+4845) rs17561G>T polymorphic locus and the IL1B (+3954) rs1143634 C>T polymorphic locus for each human subject.

Yet another aspect of the present invention relates to a method for stratifying a human population after completion of a clinical trial relating to the safety and/or efficacy of Isunakinra comprising steps of: (a) obtaining an isolated nucleic acid from a biological sample from a plurality of human subjects who have undergone a clinical trial relating to the safety and/or efficacy of Isunakinra; (b) detecting the single nucleotide polymorphism (SNP) alleles in each isolated nucleic acid for each of the IL1B (−511) rs16944 C>T polymorphic locus, the IL1B (−1464) rs1143623 G>C polymorphic locus, and the IL1B (−3737) rs4848306 C>T polymorphic locus for each human subject; (c) determining each human subject's Composite IL-1 Genetic Pattern based on the detecting in step (b) and the information disclosed in Table 1; and (d) reassessing data from the completed clinical trial relating to the safety and/or efficacy of Isunakinra for each human subject in view of each human subject's Composite IL-1 Genetic Pattern. The method may further comprise detecting the SNP alleles in each isolated nucleic acid for each of the IL1A (+4845) rs17561G>T polymorphic locus and the IL1B (+3954) rs1143634 C>T polymorphic locus for each human subject.

An aspect of the present invention relates to a method for selecting whether a human subject having allergic conjunctivitis (AC) and/or dry eye disease would receive a therapeutic benefit from or would be responsive to a treatment comprising Isunakinra comprising steps of: (a) obtaining an isolated nucleic acid from a biological sample from the human subject; (b) detecting the single nucleotide polymorphism (SNP) alleles in the isolated nucleic acid for each of the IL1B (−511) rs16944 C>T polymorphic locus, the IL1B (−1464) rs1143623 G>C polymorphic locus, and the IL1B (−3737) rs4848306 C>T polymorphic locus; (c) determining the human subject's Composite IL-1 Genetic Pattern based on the detecting in step (b) and the information disclosed in Table 1; (d) administering three times each day for at least one week to a human subject with Composite IL-1 Genetic Pattern 1 or 2 a topical ocular formulation comprising Isunakinra at a concentration of 5 mg/ml or 20 mg/ml; and (e) identifying whether a symptom of AC and/or dry eye disease that is IL-1 governing has improved and, if so, then the human subject would receive a therapeutic benefit from or would be responsive to a treatment comprising Isunakinra. The method may further comprise detecting the SNP alleles in the isolated nucleic acid for each of the IL1A (+4845) rs17561G>T polymorphic locus and the IL1B (+3954) rs1143634 C>T polymorphic locus.

Another aspect of the present invention relates to a method for treating allergic conjunctivitis (AC) and/or dry eye disease comprising steps of: (a) obtaining an isolated nucleic acid from a biological sample from the human subject; (b) detecting the single nucleotide polymorphism (SNP) alleles in the isolated nucleic acid for each of the IL1B (−511) rs16944 C>T polymorphic locus, the IL1B (−1464) rs1143623 G>C polymorphic locus, and the IL1B (−3737) rs4848306 C>T polymorphic locus; and (c) determining the human subject's Composite IL-1 Genetic Pattern based on the detecting in step (b) and the information disclosed in Table 1; and (d) administering three times a day for at least one day to a human subject with Composite IL-1 Genetic Pattern 1 or 2 a topical ocular formulation comprising Isunakinra at a concentration of 5 mg/ml or 20 mg/ml, thereby treating the AC and/or dry eye disease that is IL-1 governing. The method may further comprise detecting the SNP alleles in the isolated nucleic acid for each of the IL1A (+4845) rs17561G>T polymorphic locus and the IL1B (+3954) rs1143634 C>T polymorphic locus. When provided, the topical ocular formulation comprising Isunakinra is administered for at least one week, e.g., at least one month and at least one year.

Any aspect or embodiment described herein can be combined with any other aspect or embodiment as disclosed herein. While the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

Other features and advantages of the invention will be apparent from the following detailed description and claim.

BRIEF DESCRIPTION OF THE DRAWINGS

The above and further features will be more clearly appreciated from the following detailed description when taken in conjunction with the accompanying drawings.

DETAILED DESCRIPTION OF THE INVENTION

Figure 1:
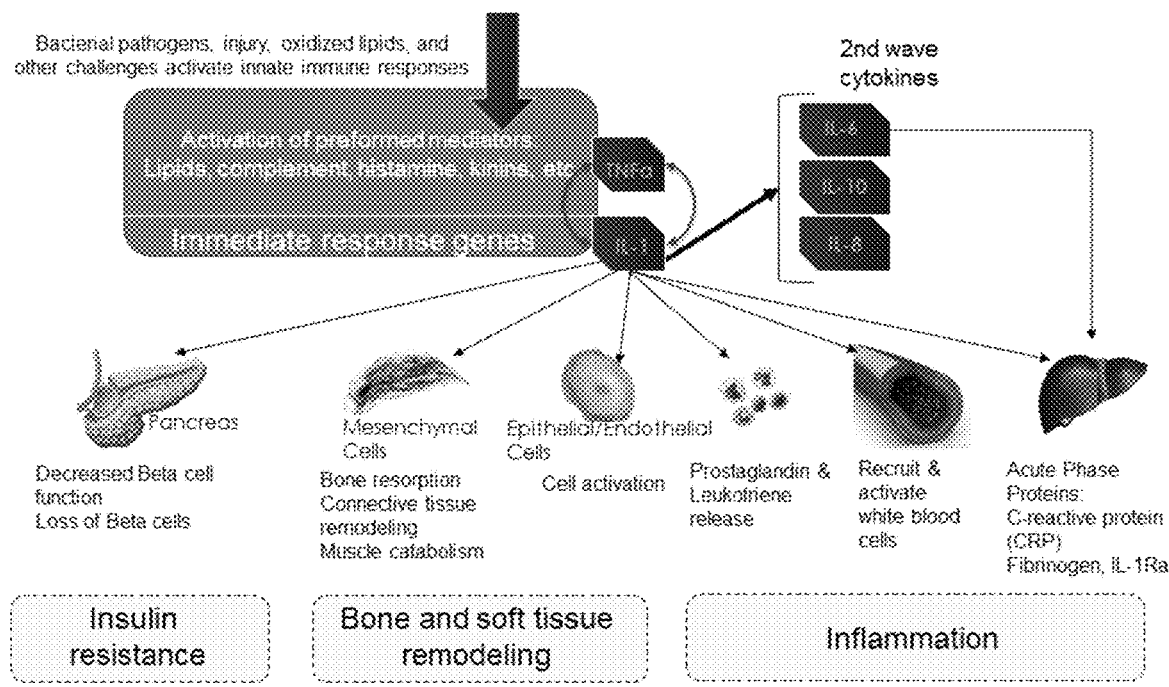
FIG. 1 is an image showing how Interleukin-1 (IL-1) drives inflammatory cascades.

The present invention provides stratification methods and kits to identify whether an individual having an inflammation-related disorder has genotype-specific differential expression of IL-1, i.e., is a "high" or "low" producer of IL-1, such that s/he can be selected to receive an appropriate anti-inflammatory drug, such as an IL-1 inhibitor, at an appropriate dose.

It has long been known that some individuals are "high producers" of IL-1 and others are "low producers". This trait is stable over time suggesting that IL-1 production is genetically linked.

The present invention is based upon the discovery of four single nucleotide polymorphisms (SNPs) in the promoter-enhancer region of the IL1B gene that are functional at the molecular level (i.e., associated with genotype-specific differential expression of IL-1) as evidenced by allele-specific differences in gene transcription in promoter-reporter constructs and allele-specific transcription factor binding. The four SNPs include IL1B (−31) rs1143627 C>T, IL1B (−511) rs16944 C>T, IL1B (−1464) rs1143623 G>C, and IL1B (−3737) rs4848306 C>T. Of the four IL1B SNPs, two SNPS (IL1B (−31) rs1143627 C>T and IL1B (−511) rs16944) C>T are in 100% linkage disequilibrium; thus, three of the SNPs capture the gene expression differences attributable to the functional haplotypes in the promoter/enhancer region of the IL1B gene. The functional haplotypes in these IL1B gene promoter/enhancer SNPs stratify the individual or a population of individuals as to whether an individual will be a "high producer" of IL-1 or a "low producer" of IL-1.

This stratification of high or low IL-1 producers is useful to guide assignment of different drug doses, which in turn should reduce drug toxicity and adverse events in an individual who, without stratification, may be prescribed a higher dose than needed to manage the primary indication. The use of IL-1 stratification of drug dosing would allow a better clinical benefit-risk appraisal in an individual patient. This stratification of high or low IL-1 producers is useful to guide specific drug selection for an individual patient.

The SNPs IL1B (−511) rs16944 C>T, IL1B (−1464) rs1143623 G>C, and IL1B (−3737) rs4848306 C>T define eight possible haplotypes, which have different frequencies in different ethnic/racial populations. Each individual will have a pair of the functional IL1B promoter/enhancer haplotypes, one of which is inherited from each parent. Accordingly, there are twenty-seven possible genotypes for the three SNP loci that one may inherit.

The present invention is further based upon the discovery that, for certain human populations (e.g., certain ethnic groups), two additional SNP loci, in conjunction with the above-mentioned IL1B gene promoter/enhancer SNPs, may contribute to a stratification as to whether an individual will be a "high producer" of IL-1 or a "low producer" of IL-1. The two additional SNP loci are IL1A (+4845) rs17561 G>T and IL1B (+3954) rs1143634 C>T.

Each of the above-mentioned SNPs may be represented in a haplotype/genotype by another SNP that is in complete linkage disequilibrium with one of the above-mentioned SNPs; thus, one, two, or three other SNPs in complete linkage disequilibrium can replace the above-mentioned SNPs in a composite genotype.

In spite of the biologic complexity of the innate immune response, it has been discovered that individuals can be stratified into one of three Composite IL-1 Genetic Patterns based upon their genotype for the three SNP loci. See, Table 1.

TABLE 1

| IL1B Haplotype pairs | IL1B (−511) rs16944 C > T | IL1B (−1464) rs1143623 G > C | IL1B (−3737) rs4848306 C > T | IL1A (+4845) rs17561 G > T | IL1B (+3954) rs1143634 C > T | Frequency (Caucasians) | IL-1β expression | Composite IL-1 Genetic Pattern |
|---|---|---|---|---|---|---|---|---|
| B1/B3 | CC | GG | CT |  |  | 17% | High | IL-1 Pattern 1 |
| B2/B3 | CT | GC | CC |  |  | 12% |  |  |
| B3/B3 | CC | GG | CC |  |  | 4% |  |  |
| B3/B4 | CT | GG | CC |  |  | 2% |  |  |
| B1/B2 | CT | GC | CT | T* | T* | 3% |  |  |
| B1/B4 | CT | GG | CT | T* | T* | <1% |  |  |
| B2/B2 | TT | CC | CC | T* | T* | 1% |  |  |
| B2/B4 | TT | CG | CC | T* | T* | <1% |  |  |
| B4/B4 | TT | GG | CC | T* | T* | <1% |  |  |
| B1/B1 | CC | GG | TT |  |  | 22% | High | IL-1 Pattern 2 |
| B1/B2 or B1/B4 | CT | G* | CT | GG / GG / T* | CC / T* / CC | 28% | Low | IL-1 Pattern 3 |
| B2/B2 or B2/B4 or B4/B4 | TT | ** | CC | GG / GG / T* | CC / T* / CC | 7% / <1% / 2% |  |  |

T* at rs17561 indicates that the second allele at that locus may be either a G or a T;
T* at rs1143634 indicates that the second allele at that locus may be either a C or a T;
G* at rs1143623 indicates that the second allele at that locus may be either a G or a C;
** at rs1143623 indicates that the genotype at that locus may be a GG, a CG, or a CC;

Two of the Composite IL-1 Genetic Patterns (Patterns 1 and 2) include individuals who, when challenged with any activator of inflammation, will be high producers of IL-1 β, and the third Composite IL-1 Genetic Patterns (Pattern 3) includes individuals who will be low producers of IL-1β. By activator of inflammation it is meant any agent or disease state that results in an inflammatory response. Activators of inflammation are well known in the art. Disease states that result in inflammation include for example but not limited to infection, cancer, autoimmune disease, arthritis, psoriasis, osteoporosis, diabetes, high blood pressure, and heart disease.

The Composite IL-1 Genetic Patterns are based on the three single nucleotide polymorphism loci that together influence IL-1 gene expression. The Composite IL-1 Genetic Patterns were derived from experimental data and expert insights that guided which haplotype pairs were clustered to form a useful pattern.

A small group of individuals are high producers of IL-1β but have different IL1B promoter haplotypes than other high producers. These individuals can be identified by the combination of allele T at IL1A (+4845), rs17561, G>T and allele T at IL1B (+3954), rs1143634, C>T. Evidence suggests these genotype patterns are tagging other functional promoter-enhancer genetic variations that influence IL-1β expression. These genotypes are included in Composite IL-1 Genetic Pattern 1.

Patterns 1 and 2 result in over-production of IL-1β by different molecular mechanisms, and therefore some diseases may predominately activate one of the two mechanisms or both. Similarly, some drugs may have a mechanism of action that results in a differential clinical response in the presence of one or more of the Composite IL-1 Genetic Patterns.

The present invention provides stratification methods and kits to identify whether an individual having an inflammation-related disorder/disease has genotype-specific differential expression of IL-1, i.e., is a "high" or "low" producer of IL-1, based upon his/her Composite IL-1 Genetic Pattern as disclosed in Table 1, such that s/he can be selected to receive an anti-inflammatory drug, such as an IL-1β inhibitor. Individuals whom are genetically determined to be a high producer of IL-1 are selected to receive an anti-inflammatory drug, such as an IL-1β inhibitor, or to receive the drug at a specific dose. In contrast, individuals whom are genetically determined to be a low producer of IL-1 are selected not to receive an anti-inflammatory drug, such as an IL-1β inhibitor, or to receive a dose of the drug different from the dose received by the high producers.

In another example, in 75 healthy human subjects, peripheral blood mononuclear cells were stimulated and IL-1β levels were determined. Pattern 3 subjects were the lowest producers of IL-1β, with mean levels of between about 0.47 and 0.56 ng/ml, Pattern 1 subjects were the highest producers of IL-1β, with mean levels of between about 1.86 and 3.25 ng/ml, and Pattern 2 subjects produced a mean level of about 2.51 ng/ml. See, e.g., Latella et al, 2009, "Interleukin 1 Gene Cluster, Myocardial Infarction at Young Age and Inflammatory Response of Human Mononuclear Cells," Immunological Investigations: A Journal of Molecular and Cellular Immunology, Vol 38, Issue 3-4, pages 203-219.

Subjects having an inflammation-related disorder include but are not limited to individuals having an inflammatory disease, a degenerative disease, an immunological disorder, an infectious disease, a trauma induced disease, or a cancer. Specific inflammation-related diseases, disorders, or conditions include but are not limited to systemic inflammatory response, Alzheimer's disease, arthritis, asthma, atherosclerosis, autoimmune myocarditis, cardiovascular disease, congestive heart failure, coronary artery disease, myocardial infarction (MI)/acute coronary syndromes, acute ischemic stroke, restenosis following coronary stenting, venous thrombosis, diabetes, gastrointestinal inflammatory disease, gastric ulcers, hepatic inflammations, HIV infection, multiple sclerosis, nephropathy, neurodegenerative disease, ophthalmic diseases including allergic conjunctivitis or dry eye syndrome, osteoporosis, chronic otitis media, pancreatitis, periodontal diseases, chronic luminary diseases, restenosis, thyroiditis, alopecia areata, Graves' disease, psoriasis, systemic lupus erythematosus, systemic sclerosis, adverse pregnancy outcomes including low birth weight, preterm delivery, generalized inflammatory response, and tissue transplant rejection. In addition, the disease, disorder, or condition may be related to periodontitis, peri-implantitis or excessive bone resorption due to orthodontic movement of teeth. The present invention relates to methods for treating or preventing, at least, any of the above-mentioned diseases, disorders, or conditions.

An anti-inflammatory drug refers to any agent or therapeutic regimen (including a pharmaceutical, biologic, nutraceutical, and botanical) that prevents or postpones the development of or alleviates a symptom of the particular disease, disorder, or condition that involved an inflammatory process in the subject. The drug can be a polypeptide, peptidomimetic, nucleic acid or other inorganic or organic molecule, a "small molecule," vitamin, mineral, or other nutrient. The drug modulates the production of the active IL-1β or IL-11α polypeptides, or at least one activity of an IL-1 polypeptide, e.g., interaction with a receptor, by mimicking or potentiating (agonizing) or inhibiting (antagonizing) the effects of a naturally-occurring polypeptide. An anti-inflammatory drug also includes, but is not limited to, anti-cholesterol drugs (e.g., statins), diabetes mellitus drugs, drugs that treat acute syndromes of the heart and vascular system (e.g., a cardiovascular disease), and arthritis.

Non-limiting examples of anti-cholesterol drugs include: Advicor, alirocumab, lovastatin (Altoprev and Mevacor), amlodipine-atorvastatin, Antara, atorvastatin, Caduet, cholestyramine, Colestid, colestipol, rosuvastatin (Crestor), Endur-Acin, evolocumab, ezetimibe, ezetimibe-simvastatin, fenofibrate, fenofibric acid (choline), fenofibric acid, Fenoglide, Fibricor, fluvastatin, fluvastatin (Lescol and Lescol XL), atorvastatin (Lipitor), Lipofen, Pitavastatin (Livalo), Lofibra, niacin, niacin-lovastatin, niacin-simvastatin, Niacor, Niaspan, Praluent, Pravastatin (Pravachol), Prevalite, Questran, Light, Questran, Repatha SureClick, Repatha Syringe, Simcor, simvastatin (Zocor), Slo-Niacin, Tricor, Triglide, Trilipix, Vytorin, and Zetia. Non-limiting examples of diabetes mellitus drugs include: acarbose, ActoplusMET, Actos, Amaryl, Avandamet, Avandia, bromocriptine, Bydureon, Byetta, Farxiga, Fortamet, glimepiride, glipizide, Glucophage, GlucophageXR, Glucovance, Glumetza, glyburide, Humalog, Invokana, Janumet, Januvia, Kombiglyze XR, Lantus, Lantus Solostar, Levemir, metformin, Novolog, NovologFlexpen, Novolog Mix70-30FlexPen, Onglyza, Parlodel, pioglitazone, Prandin, Starlix, Tradjenta, Victoza2-Pak, and WelChol. Non-limiting examples of drugs that treat acute syndromes of the heart and vascular system include: Altace, Arixtra metoprolol tartrate, aspirin, atenolol, Bystolic, BRILINTA, carvedilol, clopidogrel, Coreg, Coumadin, diovan, enoxaparin, heparin, Lisinopril, Lopressor, Lovaza, Lovenox, metoprolol tartrate, Niaspan, Nitro-Bid, nitroglycerin, Plavix, Ramipril, and warfarin. Non-limiting examples of arthritis include: Aleve, Arthrotec, aspirin, Celebrex, Cimzia, diclofenac, Enbrel, etodolac, Humira, ibuprofen, indomethacin, meloxicam, Mobic, nabumetone, naproxen, and Remicade. A drug may be useful for more than one disease or disorder associated with inflammation.

Modulators of IL-1 (e.g., IL-1α, IL-1β, or IL-1 receptor antagonist) or a protein encoded by a gene that is in linkage disequilibrium with an IL-1 gene, can comprise any type of compound, including a protein, peptide, peptidomimetic, lipid, small molecule, or nucleic acid. A modulator may be a botanical or extract of a botanical.

A modulator may indirectly act upon an IL-1 gene in that the modulator activates or represses a gene or protein that, in turn or ultimately, acts upon the IL-1 gene. By "ultimately" is meant that the modulator acts upon a first gene or protein and the first gene or protein directly acts upon the IL-1 gene or the first gene or protein acts upon a second gene or protein which directly (or indirectly) acts upon the IL-1 gene. Such indirect gene regulation is well known in the art. A modulator that acts upstream of the IL-1 gene is useful in the present invention. An example of a modulator that acts upstream of the IL-1 gene is Aldeyra's NS2 compound which traps excess free aldehydes, which are known to activate a number of intracellular inflammatory factors including NF-kB, a prominent protein in the inflammatory response. Another example of that acts upstream of the IL-1 gene is Ionis Pharmacutical's IONIS-APO(a)-$L_{Rx}$.

Alternately, a modulator may act downstream of the IL-1 gene by directly or indirectly affecting a gene or protein that operates in parallel to IL-1 in an inflammatory cascade.

An agonist can be a protein or derivative thereof having at least one bioactivity of the wild-type protein, e.g., receptor binding activity. An agonist can also be a compound that upregulates expression of a gene or which increases at least one bioactivity of a protein. An agonist can also be a compound which increases the interaction of a polypeptide with another molecule, e.g., a receptor.

An antagonist can be a compound which inhibits or decreases the interaction between a protein and another molecule, e.g., blocking the binding to receptor, blocking signal transduction, and preventing post-translation processing (e.g., IL-1 converting enzyme (ICE) inhibitor). An antagonist can also be a compound that downregulates expression of a gene or which reduces the amount of a protein present. The antagonist can be a dominant negative form of a polypeptide, e.g., a form of a polypeptide which is capable of interacting with a target. Antagonists, include nucleic acids (e.g., single (antisense) or double stranded (triplex) DNA or PNA and ribozymes), protein (e.g., antibodies) and small molecules that act to suppress or inhibit IL-1 transcription and/or protein activity.

Exemplary anti-inflammatory drugs that modulate IL-1 biological activity include for example, ABT-981, AC-701, Ammonium trichloro-tellurate, Anakinra, Anakinra Biosimilar, APX-002, Binimetinib, Can-04, Canakinumab, Diacerein, DLX-2681, Gevokizumab, Givinostat, Isunakinra, Rilonacept, RON-2315, Sairei-To, SER-140, Tadekinig-alpha, Xilonix, and XL-130. These drugs generally have a mode of action that includes modulation of IL-1 gene expression, modulation of inflammasomes, IL-1 receptor blocking agents, agents that bind IL-1β or IL-1α to inhibit attachment to the active receptor. IL-1 blocking drugs may also indirectly target IL-1 by blocking key activators of IL-1 gene expression.

A drug is prepared depending in its route of drug administration. Examples of drug administration routes that are useful in the present invention are described on the U.S. Food and Drug Administration's website at the World Wide Web (www) fda.gov/Drugs/DevelopmentApprovalProcess/FormsSubmissionRequirements/ElectronicSub missions/DataStandardsManualmonographs/ucm071667.htm.

Preparations for oral administration generally contain inert excipients in addition to the active pharmaceutical ingredient. Oral preparations may be enclosed in gelatin capsules or compressed into tablets. Common excipients used in such preparations include pharmaceutically compatible fillers/diluents such as microcrystalline cellulose, hydroxypropyl methylcellulose, starch, lactose, sucrose, glucose, mannitol, sorbitol, dibasic calcium phosphate, or calcium carbonate; binding agents such as alginic acid, carboxymethylcellulose, microcrystalline cellulose, gelatin, gum tragacanth, or polyvinylpyrrolidone; disintegrating agents such as alginic acid, cellulose, starch, or polyvinylpyrrolidone; lubricants such as calcium stearate, magnesium stearate, talc, silica, or sodium stearyl fumarate; glidants such as colloidal silicon dioxide; sweetening agents such as sucrose or saccharin; flavoring agents such as peppermint, methyl salicylate, or citrus flavoring; coloring agents; and preservatives such as antioxidants (e.g., vitamin A, vitamin C, vitamin E, or retinyl palmitate), citric acid, or sodium citrate. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as ethylenediaminetetraacetic acid (EDTA); a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

For topical (e.g., transdermal or transmucosal) administration, penetrants appropriate to the barrier to be permeated are generally included in the preparation. Transmucosal administration may be accomplished through the use of nasal sprays, aerosol sprays, tablets, or suppositories, and transdermal administration may be via ointments, salves, gels, patches, or creams as generally known in the art. Topical ocular formulations, e.g., eye drops and eye ointments, are considered.

The amount of agent that is administered to the subject can and will vary depending upon the type of agent, the subject, and the particular mode of administration. Those skilled in the art will appreciate that dosages may also be determined with guidance from Goodman & Gilman's The Pharmacological Basis of Therapeutics, Twelfth Edition (2011), Appendix II, pp. 1891-1991, and the Physicians' Desk Reference $70^{th}$ Edition, 2016.

Pharmacogenomics

Pharmacogenomics is the methodology which associates genetic variability with physiological and clinical responses to a drug. Pharmacogenetics is a subset of pharmacogenomics and is defined as "the study of variations in DNA sequence as related to drug response" (ICH E15; see the World Wide Web (www) fda.gov/downloads/RegulatoryInformation/Guidances/ucm129296.pdf). Pharmacogenetics often focuses on genetic polymorphisms in genes related to drug metabolism, drug mechanism of action, underlying disease type, and drug associated side effects. Pharmacogenetics is the cornerstone of Personalized Medicine which allows the development and the targeted use of drug therapies to obtain effective and safe treatment, as well as to adjust existing treatment regimens to further optimize the efficacy and safety profile for the individual patient.

Pharmacogenetics has become a core component of many drug development programs, being used to explain variability in drug response among subjects in clinical trials, to address unexpected emerging clinical issues, such as adverse events, to determine eligibility for a clinical trial (pre-screening) to optimize trial yield, to develop drug companion diagnostic tests to identify patients who are more likely or less likely to benefit from treatment or who may be at risk of adverse events, to provide information in drug labels to guide physician treatment decisions, to better understand the mechanism of action or metabolism of new and existing drugs, and to provide better understanding of disease mechanisms as associated with treatment response.

Generally, pharmacogenetics analyses are often performed using the candidate genes research technique, which is a hypothesis-driven approach, based on the detection of polymorphisms in candidate genes pre-selected using knowledge of the disease, the drug's mode of action, toxicology, or metabolism of the drug.

In the present invention, using the candidate genes research technique, a subject has his/her Composite IL-1 Genotype Pattern determined (as disclosed herein) before an initial treatment and/or after a treatment has begun to determine a therapeutic strategy based upon the individual's genotype. An individual may be administered a higher dose or a lower dose (e.g., the dose of a single treatment and/or a daily dose comprising one or more single treatments) of a particular drug depending on his/her Composite IL-1 Genotype Pattern; alternately, the individual may be not given the particular drug depending on his/her Composite IL-1 Genotype Pattern and instead may be administered another drug. For example, the other drug may operate by a different mode of action.

Exemplary IL-1-related drugs, their modes of action, and disease/disorder indications are listed below in Table 2.

TABLE 2

Agents that inhibit IL-1 biologic activity
Mode of action (MOA)
Bind directly to IL-1α or IL-1β to block binding to their receptor and modulate cell signaling events that lead to inflammation

| | Example Drugs | | | |
|---|---|---|---|---|
| | Drug name | Company | Delivery route | Example Indications |
| Human monoclonal antibody against IL-1α | Xilonix | XBiotech | Injectable: IV, or sub Q | Acne, Atherosclerosis, Colorectal cancer, Hematological malignancies, Rheumatoid arthritis |
| Human monoclonal antibody against IL-1β blocks activation of the IL-1 receptor | Gevokizumab | Xoma/Servier | Injectable: IV, or sub Q | Type 2 diabetes, Rheumatoid arthritis, Systemic Juvenile Idiopathic Arthritis |
| Human monoclonal dual variable domain antibody that neutralizes IL-1α and IL-1β. | ABT-981 | Abbott/Abbvie | Injectable: IV, or sub Q | Rheumatoid arthritis, Osteoarthritis |
| Human monoclonal antibody against interleukin-1β | Canakinumab | Novartis | Injectable: IV, Sub Q, or Intra-articular | Cryopyrin-associated periodic syndrome, Familial Cold Autoinflammatory Syndrome, Muckle-Wells Syndrome, Systemic Juvenile Idiopathic Arthritis, Neonatal onset multisystem inflammatory disease, Arthritis, gouty, Arthritis, juvenile, Hyperuricaemia, Atherosclerosis, Secondary cardiovascular events, Familial Mediterranean fever, Chronic obstructive pulmonary disease, Osteoarthritis, Xerophthalmia, Polymyalgia rheumatica, TNF receptor associated periodic syndrome, Intermittent claudication, Pain, musculoskeletal, arthritis, Peripheral vascular disease, Aneurysm, Diabetic complications, Asthma, Diabetes, Type 2, Diabetes, Type 1, Rheumatoid arthritis, Macular degeneration, age-related, wet, |

TABLE 2-continued

| | | | | |
|---|---|---|---|---|
| Human monoclonal antibody against IL-1β, IL1B antagonist | DLX-2681 | Delenex Therapeutics | Injectable Topical | Acne, Gouty Arthritis, Hidradenitis Suppurativa |
| Human monoclonal antibody against Anti-IL-1β | APX-002 | Apexigen | Injectable | Inflammatory disease, Gout, Diabetes, undisclosed Type, Hyperuricaemia |
| Recombinant human fusion protein. Interleukin 1α and β antagonist by blocking (competing) binding with its receptor | Isunakinra | Eleven Biotherapeutics | Topical | Dry Eye Disease, Allergic Conjunctivitis |

| Mode of action (MOA) IL-1 Receptor Antagonist | Drug name | Company | Delivery route | Example Indications |
|---|---|---|---|---|
| Recombinant Human Protein Interleukin 1β antagonist | Anakinra | Amgen/Swedish Orphan Biovitrum (SOBi) | Injectable: IV Sub Q, or Intra-articular | Familial cold auto-inflammatory syndrome, Muckle-Wells syndrome, Arthritis, juvenile Anemia, renal disease-induced Osteoarthritis Thrombophlebitis Hyperuricaemia Arthritis, Rheumatoid Neonatal-Onset Multisystem Inflammatory Disease (NOMID), Adult onset Still's Disease |
| IL-1 receptor antagonist | SER-140 | Serodus | Injectable | Type 2 Diabetes |
| Recombinant human protein interleukin 1 receptor antagonist | Anakinra Biosimilar | Paras Biopharmaceuticals Finland | Injectable: Sub Q | Rheumatoid Arthritis |

| Mode of action (MOA) Inflammasome modulator | Drug name | Company | Delivery route | Example Indications |
|---|---|---|---|---|
| Inflammasome modulators that inhibit IL-1β | | Opsona | Oral | Arthritis, Rheumatoid Asthma, Hperuricaemia, Diabetes (undisclosed type) |
| IL-12/23 antagonist | RON-2315 | ISIS Innovation/Rogne Bioscience | Topical | Psoriasis, Gastrointestinal disease, Ocular disorder, Respiratory disease |
| IL-1B Inhibitor | Diacerein | TWI Pharmaceuticals | Oral Topical | Type 2 Diabetes, Hyperuricemia, Epidermolysis Bullosa, Osteoarthritis |
| Interleukin 1a antagonist | AC-701 | TWI Pharmaceuticals | Topical | Rosacea, cancer-therapy-induced skin rash |
| Kampo (Japanese herbal) that induces the interleukin-1 receptor antagonist (IL-1ra). Interleukin 1 antagonist | Sairei-To | Tsumura | Oral | Nephritis, Rheumatoid Arthritis |
| MEK inhibitor Interleukin 1b antagonist MAP kinase inhibitor | binimetinib | Array BioPharma | Oral | Cancer, fallopian tube, Cancer, ovarian, Cancer, peritoneal, Cancer, colorectal, Rheumatoid arthritis, Chronic obstructive pulmonary disease, Inflammatory bowel disease |
| IL-1β inhibitor | Unspecified | Novartis | Injectable | Hypercholesterolaemia |
| Anti-interleukin-1 receptor accessory protein (IL1RAP) MAb | Can-04 | Cantargia | Injectable | Cancer, Leukemia, Chronic myelogenous |

TABLE 2-continued

| | | | | |
|---|---|---|---|---|
| Interleukin-1 inhibitor | N/A | Affibody/ Swedish Orphan Biovitrum | Injectable | Autoimmune diseases |
| Interleukin 1b antagonist | Rilonacept | Regeneron | Injectable: Sub Q | Cryopyrin-associated periodic syndromes (CAPS), Familial cold autoinflammatory syndrome (FCAS), Muckle-Wells syndrome (MWS), Osteoarthritis, Rheumatoid arthritis, Juvenile arthritis |
| Recombinant human interleukin 18 binding protein inhibitor | Tadekinig-alpha | AB2 Bio | Injectable: Sub Q | Adult -onset Still's disease (AoSD) |
| Interleukin 1 receptor antagonist (IL-1Ra) | XL-130 | XL-protein | Injectable | Rheumatoid arthritis |
| Reduces expression of tumour necrosis factor (TNF), interleukin 1α and β, and interleukin 6. | Givinostat | Italfarmaco | Oral | Juvenile idiopathic arthritis, Duchenne Muscular Dystrophy and Becker Muscular Dystrophy |
| Interleukin 17 antagonist Interleukin 1beta converting enzyme inhibitor Interleukin 18 antagonist Interleukin 17 receptor antagonist | Ammonium trichloro-tellurate | Biomas | Injectable Topical | Infection, human papilloma virus, Infection, HIV/AIDS, Psoriasis, Clin-Radio/chemotherapy-induced alopecia, Clin- Eczema, atopic |

Any of the drugs listed in Table 2 may be used in the present invention. In other words, an individual may be administered a drug of Table 2 a higher dose or at a lower dose (e.g., the dose of a single treatment and/or a daily dose comprising one or more single treatments) depending on his/her Composite IL-1 Genotype Pattern; alternately, the individual may be not given the particular drug depending on his/her Composite IL-1 Genotype Pattern and instead may be administered a different drug. For example, rather than being administered Xilonix, which is a human monoclonal antibody against IL-1α, based on the individual's Composite IL-1 Genotype Pattern, the individual may be administered Gevokizumab, which is a human monoclonal antibody against IL-1β.

Additionally, drugs other than those listed in Table 2 may be used in the present invention. For this, an alternate drug having a mode of action (MOA) similar to or identical to a drug listed in Table 2 may be provided instead of or in addition to the drug listed in Table 2. For example, Table 2 identifies Canakinumab as a human monoclonal antibody against interleukin-1β for treating cryopyrin-associated periodic syndromes; in the present invention, a subject's Composite IL-1 Genotype Pattern may be used for the selection of and preferred dose of Canakinumab and/or other human monoclonal antibodies directed against interleukin-1β for treating cryopyrin-associated periodic syndromes.

A subject may be provided a drug from Table 2 or an alternate drug having a MOA similar to or identical to a drug listed in Table 2 at the standard therapeutic dose. The drug may be given at a dose lower than the standard therapeutic dose, e.g., 99%, 95%, 90%, 85%, 80%, 75%, 70%, 60%, 50%, 40%, 30%, 20%, 15%, 10%, or 5%, and any percentage in between lower than the standard therapeutic dose. The drug may be given at a dose higher than the standard therapeutic dose, e.g., 5%, 10%, 15%, 20%, 30%, 40%, 50%, 60%, 70%, 75%, 80%, 85%, 90%, 95%, 100%, 125%, 150%, 175%, 200%, 300%, 400%, 500%, 600%, 700%, 800%, 900%, 1000%, 2000%, or more, and any percentage in between higher than the standard therapeutic dose. For example, if a standard therapeutic dose is 10 mg per day, a subject may be given 7 mg per day as a lower than standard therapeutic dose or 13 mg per day as a higher than standard therapeutic dose.

In a non-limiting example, the drug used in the present invention is Isunakinra (Eleven Biotherapeutics, Inc., Cambridge, Mass., USA) for the treatment of allergic conjunctivitis (AC) and/or dry eye disease. Isunakinra is provided as a topical, eye-drop formulation. Isunakinra may be formulated at about 5 mg/ml (e.g., about 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, and any concentration in between). Isunakinra may be formulated at about 20 mg/ml (e.g., about 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 30 mg/ml, 40 mg/ml, 50 mg/ml, and any concentration in between). A subject in need may be provided Isunakinra once per day, twice per day, thrice per day, four times per day, five times per day, or more times per day. A single drop of the Isunakinra formulation may be provided each time to an eye or a plurality of drops (e.g., two drops, three drops, four drops, five drops, or more) may be provided each time. A subject may receive the Isunakinra for a day or more, e.g., a week, a month, a year, or more. A subject may increase or decrease the frequency of treatments per day and/or increase or decrease the concentration of an Isunakinra formulation depending on his/her Composite IL-1 Genotype Pattern, as described herein. "More aggressive" therapeutic regimen includes increased frequency and/or increased concentration of Isunakinra relative to "less aggressive" therapeutic regimen.

Using Isunakinra as an example, a subject in need of treatment for AC and/or dry eye disease that is IL-1 governing will provide or had provided a biological sample comprising a nucleic acid. Single nucleotide polymorphism (SNP) alleles in the isolated nucleic acid for each of the IL1B (−511) rs16944 C>T polymorphic locus, the IL1B (−1464) rs1143623 G>C polymorphic locus, and the IL1B (−3737) rs4848306 C>T polymorphic locus will be detected by any method known in the art and a Composite IL-1 Genotype Pattern determined based on the information disclosed in Table 1 will be determined. The subject may then be provided a therapeutic regimen comprising Isunakinra and/or provided a recommendation for a therapeutic regimen comprising Isunakinra that is selected based upon his/her Composite IL-1 Genotype Pattern. For example, a subject having a Composite IL-1 Genetic Pattern 1 or 2 would be provided or recommended a more aggressive (e.g., higher dose) therapeutic regimen comprising Isunakinra relative to a subject with Composite IL-1 Genetic Pattern 3, who may receive a therapeutic regimen not comprising Isunakinra.

A human subject with Composite IL-1 Genetic Pattern 1 or Pattern 2 may have his allergic conjunctivitis (AC) and/or dry eye disease that is IL-1 governing treated by being administered three times a day for at least one day (e.g., at least one day, at least one week, at least one month, and at least one year) a topical ocular formulation comprising Isunakinra at a concentration of 5 mg/ml or 20 mg/ml.

Additionally, using Isunakinra as an example, the present invention provides methods for predicting whether a human subject with allergic conjunctivitis (AC) and/or dry eye disease delete would receive a therapeutic benefit from/would be responsive to Isunakinra. Here, the subject provides a biological sample or had provided a biological sample comprising a nucleic acid. SNP alleles in the isolated nucleic acid for each of the IL1B (−511) rs16944 C>T polymorphic locus, the IL1B (−1464) rs1143623 G>C polymorphic locus, and the IL1B (−3737) rs4848306 C>T polymorphic locus will be detected by any method known in the art and a Composite IL-1 Genotype Pattern determined based on the information disclosed in Table 1 will be determined. A subject having a Composite IL-1 Genetic Pattern 1 or 2 would more likely have AC and/or dry eye disease that is IL-1 governing whereas a subject with Composite IL-1 Genetic Pattern 3 would less likely have AC and/or dry eye disease that is IL-1 governing. Moreover, a subject having a Composite IL-1 Genetic Pattern 1 or 2 would likely receive a therapeutic benefit from/would be responsive to Isunakinra whereas a subject with Composite IL-1 Genetic Pattern 3 would less likely receive a therapeutic benefit from/would be responsive to Isunakinra.

The present invention also provides methods for selecting whether a human subject having AC and/or dry eye disease that is IL-1 governing would receive a therapeutic benefit from or would be responsive to a treatment comprising Isunakinra. For this, a human subject with Composite IL-1 Genetic Pattern 1 or Pattern 2 is administered three times a day for at least one week a topical ocular formulation comprising Isunakinra at a concentration of 5 mg/ml or 20 mg/ml. After 1 week, the subject is evaluated to determine whether a symptom of the AC and/or dry eye disease that is IL-1 governing has improved, and if so, then the human subject is predicted to receive a therapeutic benefit from or would be responsive to a treatment comprising Isunakinra.

Alternately, the present invention may be used to optimize the size of a clinical trial. For this, a study population is stratified by Composite IL-1 Genotype Pattern during or before randomization. This way, each group in a study will have sufficient numbers of members from each Pattern. This allows for smaller-sized groups which can nonetheless be informative and provide statistical significance. For example, based on experimental data (described in the Examples and not shown) to adequately populate each of the three Composite IL-1 Genotype Patterns such that a predictive genetic effect is revealed, only twenty to thirty subjects per Pattern are needed. Given the Pattern frequencies disclosed in Table 1, a total population size will include only 150 (Caucasian or Hispanic) subjects to populate approximately thirty subjects in Pattern 2 (the least frequent Pattern); this would leave fifty to seventy subjects in each of Patterns 1 and 3. Non-Caucasian ethnic/racial groups have different frequencies for each pattern; thus, study populations comprising Non-Caucasians may need to have their total population size adjusted accordingly. When a population is not stratified, the treatment population will include subjects who are non-responders to a treatment (based on their IL-1β expression and due to their Composite IL-1 Genotype Pattern). When these non-responders fail to respond to the treatment, then the overall response rate to the treatment will be reduced. In certain clinical trials, when the non-responders mask the positive response of subjects with other Composite IL-1 Genotype Patterns (whose IL-1β expression is compatible with the treatment's mode of action), the effect of the non-responders skews the ultimate results against an overall positive effect to the treatment. Thus, when subjects are stratified in a clinical trial by Composite IL-1 Genotype Patterns, it is possible to obtain more accurate or reliable data when compared to a clinical trial in which subjects are not stratified by Composite IL-1 Genotype Patterns.

Such stratification of clinical trial subjects may occur any time before, during, or after the clinical trial. In the latter case, for example, if a clinical trial does not provide statistical significance using a general, non-stratified population, true statistical significant may be later be discovered when the subject data is reconsidered and stratified by Composite IL-1 Genotype Pattern. That is, if the data of the clinical did not show statistical evidence of a treatment response (due to inclusion in the population of non-responders whose IL-1β expression is incompatible with the treatment's mode of action), the data could later be revaluated with consideration of Composite IL-1 Genotype Patterns. If so, it is possible that a previously "unsuccessful" clinical trial could be made "successful" when subjects are retroactively stratified by Composite IL-1 Genotype Pattern.

When subjects are stratified by Composite IL-1 Genotype Pattern, subjects of certain Patterns who will benefit from the treatment are identified and subjects of other Patterns who will not benefit (or benefit less) from the treatment are identified. Once the treatment is approved for clinical use, the stratified clinical trials will have revealed which patient populations (i.e., patients with a specific Composite IL-1 Genotype Pattern) should be provided the treatment and which patients should not.

For example, subjects in a clinical trial directed to the efficacy of Isunakinra may be stratified by Composite IL-1 Genotype Pattern. Stratification may occur before the clinical trial has begun such that each subject is assigned into a study group based on his/her Composite IL-1 Genetic Pattern. Alternately, stratification may occur after the clinical trial has begun (e.g., after its conclusion) such that obtained data can be can be assessed or reassessed based upon a subject's Composite IL-1 Genetic Pattern. Subjects in such a clinical trial may have, may be suspected of having, or at risk for having an IL-1 governing allergic conjunctivitis (AC) and/or dry eye disease. After stratification, data from subjects with Composite IL-1 Genotype Pattern 1 or 2 may be compared to data from subjects with Composite IL-1 Genotype Pattern 3.

The present invention, in view of the disclosures of Table 1 and Table 2, allow a skilled artisan to identify:
1. Subjects likely to derive more benefit from specific drug;
2. Subjects with one pattern who may respond favorably to lower levels of the drug than subjects of a different pattern;
3. Subjects who should be on an IL-1-blocking drug earlier than others because their genotype pattern is more aggressive; and
4. Subjects with an IL-1 dominant disease subtype that may be predictably responsive to IL-1-blocking drugs but not other agents which have different modes of action.

The present invention allows differentiation of an individual (and thus his treatment regimen) who has a generalized inflammatory disorder that may be the result of multiple causes. For example, clinical osteoarthritis may be a collection of multiple subsets that have different "causes". A subject's Composite IL-1 Genotype Pattern will identify whether s/he has an IL-1directed osteoarthritis and, if so, that s/he would be responsive to an IL-1 blocking agent.

Determining a subject's Composite IL-1 Genotype Pattern requires detecting the identity of SNPs in an isolated nucleic acid molecule ultimately obtained or derived from the subject.

Isolated Nucleic Acid Molecules

As used herein, an "isolated nucleic acid molecule" generally is one that contains one or more of the SNPs disclosed herein or one that hybridizes to such molecule such as a nucleic acid with a complementary sequence, and is separated from most other nucleic acids present in the natural source of the nucleic acid molecule. As used herein, "a non-naturally occurring nucleic acid molecule" generally is one that contains one or more of the SNPs disclosed herein or one that hybridizes to such a molecule, such as a nucleic acid with a complementary sequence, but which does not correspond to a naturally occurring molecule, e.g., it can be a molecule prepared by recombinant nucleic acid technology, chemical synthesis, or other synthetic means such as polymerase chain reaction (PCR), and/or a nucleic acid which comprises one or more synthetic components such as a non-natural nucleotide or an added tag/motif.

The isolated nucleic acid may be obtained from any bodily fluid (such as blood, serum, plasma, urine, saliva, phlegm, gastric juices, semen, tears, sweat, etc.), skin, hair, cell (especially nucleated cells), biopsy, buccal swab, tissue, or tumor specimen. Alternately, the isolated nucleic acid may be amplified or synthesized from a nucleic acid obtained from any bodily fluid, skin, hair, cell, biopsy, buccal swab, tissue, or tumor specimen.

Generally, an isolated SNP-containing nucleic acid molecule includes one or more of SNPs IL1B (−31) rs1143627 C>T, IL1B (−511) rs16944 C>T, IL1B (−1464) rs1143623 G>C, and IL1B (−3737) rs4848306 C>T or one or more SNP in complete linkage disequilibrium with one of the four above-mentioned IL1B SNPs. The isolated SNP-containing nucleic acid molecule may include flanking nucleotide sequences on either side of the SNP position. A flanking sequence can include nucleotide residues that are naturally associated with the SNP site and/or heterologous nucleotide sequences. Preferably, the flanking sequence is up to about 10,000, 1,000, 500, 300, 100, 60, 50, 30, 25, 20, 15, 10, 8, or 4 nucleotides (or any other length in-between) on either side of a SNP position, or as long as the full-length gene, entire protein-coding sequence (or any portion thereof such as an exon), entire enhancer/promoter region or portion thereof, or entire intron or portion thereof.

An isolated SNP-containing nucleic acid molecule can include, for example, a full-length gene or transcript, such as a gene isolated from genomic DNA (e.g., by cloning or PCR amplification), a cDNA molecule, or an mRNA transcript molecule.

An isolated nucleic acid molecule of the disclosed subject matter further encompass a SNP-containing polynucleotide that is the product of any one of a variety of nucleic acid amplification methods, which are used to increase the copy numbers of a polynucleotide of interest in a nucleic acid sample. Such amplification methods are well known in the art, and they include but are not limited to, polymerase chain reaction (PCR) (U.S. Pat. Nos. 4,683,195 and 4,683,202; PCR Technology: Principles and Applications for DNA Amplification, ed. H. A. Erlich, Freeman Press, NY, N.Y. (1992)), ligase chain reaction (LCR) (Wu and Wallace, Genomics 4:560 (1989); Landegren et al., Science 241:1077 (1988)), strand displacement amplification (SDA) (U.S. Pat. Nos. 5,270,184 and 5,422,252), transcription-mediated amplification (TMA) (U.S. Pat. No. 5,399,491), linked linear amplification (LLA) (U.S. Pat. No. 6,027,923) and the like, and isothermal amplification methods such as nucleic acid sequence based amplification (NASBA) and self-sustained sequence replication (Guatelli et al., Proc Natl Acad Sci USA 87:1874 (1990)). Based on such methodologies, a person skilled in the art can readily design primers in any suitable regions 5' and 3' to a SNP disclosed herein. Such primers may be used to amplify DNA of any length so long that it contains the SNP of interest in its sequence.

The isolated nucleic acid molecules that include, consist of, or consist essentially of one or more polynucleotide sequences that contain one or more SNPs disclosed herein, complements thereof, and/or SNP-containing fragments thereof.

Isolated nucleic acid molecules can be in the form of RNA, such as mRNA, or in the form DNA, including cDNA and genomic DNA, which may be obtained, for example, by molecular cloning or produced by chemical synthetic techniques or by a combination thereof. Sambrook and Russell, Molecular Cloning: A Laboratory Manual, Cold Spring Harbor Press, N.Y. (2000). Furthermore, isolated nucleic acid molecules, particularly SNP detection reagents such as probes and primers, can also be partially or completely in the form of one or more types of nucleic acid analogs, such as peptide nucleic acid (PNA). U.S. Pat. Nos. 5,539,082; 5,527,675; 5,623,049; and 5,714,331. The nucleic acid, especially DNA, can be double-stranded or single-stranded. Single-stranded nucleic acid can be the coding strand (sense strand) or the complementary non-coding strand (anti-sense strand). DNA, RNA, or PNA segments can be assembled, for example, from fragments of the human genome (in the case of DNA or RNA) or single nucleotides, short oligonucleotide linkers, or from a series of oligonucleotides, to provide a synthetic nucleic acid molecule. Nucleic acid molecules can be readily synthesized using the sequences provided herein as a reference; oligonucleotide and PNA oligomer synthesis techniques are well known in the art. See, e.g., Corey, "Peptide nucleic acids: expanding the scope of nucleic acid recognition," Trends Biotechnol 15 (6):224-9 (June 1997), and Hyrup et al., "Peptide nucleic acids (PNA): synthesis, properties and potential applications," Bioorg Med Chem 4 (1):5-23 (January 1996). Furthermore, large-scale automated oligonucleotide/PNA synthesis (including synthesis on an array or bead surface or other solid support) can readily be accomplished using commercially available nucleic acid synthesizers, such as the Applied Biosystems (Foster City, Calif.) 3900 High-Throughput DNA Synthesizer or Expedite 8909 Nucleic Acid Synthesis System and the sequence information provided herein.

The isolated SNP-containing nucleic acid molecule may comprise modified, synthetic, or non-naturally occurring nucleotides or structural elements or other alternative/modified nucleic acid chemistries known in the art. Such nucleic acid analogs are useful, for example, as detection reagents (e.g., primers/probes) for detecting the SNPs identified herein. Furthermore, kits/systems (such as beads, arrays, etc.) that include these analogs are also encompassed herein.

The practice of the present methods will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning: A Laboratory Manual, Cold Spring Harbor Laboratory (2001); DNA Cloning, Volumes I and II (P. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. Q. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu at al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

SNP Detection Reagents

In aspects of the present invention, each of the one or more of the SNPs disclosed herein can be used for the design of SNP detection reagents. As used herein, a "SNP detection reagent" is a reagent that specifically detects a specific target SNP position disclosed herein, and that is preferably specific for a particular nucleotide (allele) of the target SNP position (i.e., the detection reagent preferably can differentiate between different alternative nucleotides at a target SNP position, thereby allowing the identity of the nucleotide present at the target SNP position to be determined). Typically, such detection reagent hybridizes to a target SNP-containing nucleic acid molecule by complementary base-pairing in a sequence specific manner, and discriminates the target variant sequence from other nucleic acid sequences such as an art-known form in a test sample. An example of a detection reagent is a non-naturally occurring nucleic acid probe that hybridizes to a target nucleic acid containing one of the SNPs disclosed herein. In a preferred embodiment, such a probe can differentiate between nucleic acids having a particular nucleotide (allele) at the target SNP position from other nucleic acids that have a different nucleotide at the same target SNP position. In addition, a detection reagent may hybridize to a specific region 5' and/or 3' to the SNP position.

Another example of a detection reagent is a non-naturally occurring nucleic acid primer that acts as an initiation point of nucleotide extension along a complementary strand of a target polynucleotide. The SNP sequence information provided herein is also useful for designing primers, e.g., allele-specific primers, to amplify (e.g., using PCR) the SNP of the disclosed subject matter.

A SNP detection reagent may be an isolated or synthetic DNA or RNA polynucleotide probe or primer or PNA oligomer, or a combination of DNA, RNA and/or PNA that hybridizes to a segment of a target nucleic acid molecule containing one of the SNPs disclosed herein. A detection reagent in the form of a non-naturally occurring polynucleotide may optionally contain modified base analogs, intercalators, or minor groove binders. Multiple detection reagents such as probes may be, for example, affixed to a solid support (e.g., an array and bead) or supplied in solution (e.g., probe/primer sets for enzymatic reactions such as PCR, RT-PCR, TaqMan® assays, and primer-extension reactions) to form a SNP detection kit.

For analyzing SNPs, it can be appropriate to use oligonucleotides specific for alternative SNP alleles. Such oligonucleotides that detect single nucleotide variations in target sequences may be referred to by such terms as "allele-specific oligonucleotides," "allele-specific probes," or "allele-specific primers." The design and use of allele-specific probes for analyzing polymorphisms is described in, e.g., Mutation Detection: A Practical Approach, Cotton et al., eds., Oxford University Press (1998); Saiki et al., Nature 324:163-166 (1986); Dattagupta, EP235,726; and Saiki, WO 89/11548.

In another embodiment, a probe or primer may be designed to hybridize to a segment of target DNA such that the SNP aligns with either the 5'-most end or the 3'-most end of the probe or primer. When using an oligonucleotide ligation assay (U.S. Pat. No. 4,988,617), the 3' most nucleotide of the probe aligns with the SNP position in the target sequence.

Allele-specific probes are often used in pairs (or, less commonly, in sets of 3 or 4), and such pairs may be identical except for a one nucleotide mismatch that represents the allelic variants at the SNP position. Typically, one member of a probe pair perfectly matches a reference form of a target sequence that has a more common SNP allele (i.e., the allele that is more frequent in the target population) and the other member of the pair perfectly matches a form of the target sequence that has a less common SNP allele (i.e., the allele that is rarer in the target population). In the case of an array, multiple pairs of probes can be immobilized on the same support for simultaneous analysis of multiple different polymorphisms.

In one type of PCR-based assay, an allele-specific primer hybridizes to a region on a target nucleic acid molecule that overlaps a SNP position and only primes amplification of an allelic form to which the primer exhibits perfect complementarity. Gibbs, Nucleic Acid Res 17:2427-2448 (1989). Typically, the primer's 3'-most nucleotide is aligned with and complementary to the SNP position of the target nucleic acid molecule. This primer is used in conjunction with a second primer that hybridizes at a distal site. Amplification proceeds from the two primers, producing a detectable product that indicates which allelic form is present in the test sample. A control is usually performed with a second pair of primers, one of which shows a single base mismatch at the polymorphic site and the other of which exhibits perfect complementarity to a distal site. The single-base mismatch prevents amplification or substantially reduces amplification efficiency, so that either no detectable product is formed or it is formed in lower amounts or at a slower pace. The method generally works most effectively when the mismatch is at the 3'-most position of the oligonucleotide (i.e., the 3'-most position of the oligonucleotide aligns with the target SNP position) because this position is most destabilizing to elongation from the primer (see, e.g., WO 93/22456). This PCR-based assay can be utilized as part of the TaqMan® assay, described below.

A primer may contain a sequence substantially complementary to a segment of a target SNP-containing nucleic acid molecule except that the primer has a mismatched nucleotide in one of the three nucleotide positions at the 3'-most end of the primer, such that the mismatched nucleotide does not base pair with a particular allele at the SNP site. In a preferred embodiment, the mismatched nucleotide in the primer is the second from the last nucleotide at the 3'-most position of the primer. In a more preferred embodiment, the mismatched nucleotide in the primer is the last nucleotide at the 3'-most position of the primer.

A SNP detection reagent may be labeled with a fluorogenic reporter dye that emits a detectable signal. While the preferred reporter dye is a fluorescent dye, any reporter dye that can be attached to a detection reagent such as an oligonucleotide probe or primer is suitable for use in the disclosed subject matter. Such dyes include, but are not limited to, Acridine, AMCA, BODIPY, Cascade Blue, Cy2, Cy3, Cy5, Cy7, Dabcyl, Edans, Eosin, Erythrosin, Fluorescein, 6-Fam, Tet, Joe, Hex, Oregon Green, Rhodamine, Rhodol Green, Tamra, Rox, and Texas Red.

In yet another embodiment, the detection reagent may be further labeled with a quencher dye such as Tamra, especially when the reagent is used as a self-quenching probe such as a TaqMan® (U.S. Pat. Nos. 5,210,015 and 5,538,848) or Molecular Beacon probe (U.S. Pat. Nos. 5,118,801 and 5,312,728), or other stemless or linear beacon probe (Livak et al., PCR Method Appl 4:357-362 (1995); Tyagi et al., Nature Biotechnology 14:303-308 (1996); Nazarenko et al., Nuc' Acids Res 25:2516-2521 (1997); U.S. Pat. Nos. 5,866,336 and 6,117,635.

Detection reagents may also contain other labels, including but not limited to, biotin for streptavidin binding, hapten for antibody binding, and an oligonucleotide for binding to another complementary oligonucleotide.

Reagents may not contain (or be complementary to) a SNP nucleotide as describe herein but that are used to assay one or more SNPs disclosed herein. For example, primers that flank, but do not hybridize directly to a target SNP position provided herein are useful in primer extension reactions in which the primers hybridize to a region adjacent to the target SNP position (i.e., within one or more nucleotides from the target SNP site). During the primer extension reaction, a primer is typically not able to extend past a target SNP site if a particular nucleotide (allele) is present at that target SNP site, and the primer extension product can be detected in order to determine which SNP allele is present at the target SNP site. For example, particular ddNTPs are typically used in the primer extension reaction to terminate primer extension once a ddNTP is incorporated into the extension product (a primer extension product which includes a ddNTP at the Y-most end of the primer extension product, and in which the ddNTP is a nucleotide of a SNP disclosed herein, is a composition that is specifically herein). Thus, reagents that bind to a nucleic acid molecule in a region adjacent to a SNP site and that are used for assaying the SNP site, even though the bound sequences do not necessarily include the SNP site itself, are also contemplated by the disclosed subject matter.

For example, the SNP may be identified using single-base extension (SBE). SBE determines the identity of a nucleotide base at a specific position along a nucleic acid. In the method, an oligonucleotide primer hybridizes to a complementary region along the nucleic acid, to form a duplex, with the primer's terminal 3' end directly adjacent to the nucleotide base to be identified. The oligonucleotide primer is enzymatically extended by a single base in the presence of all four nucleotide terminators; the nucleotide terminator complementary to the base in the template being interrogated is incorporated and identified. The presence of all four terminators ensures that no further extension occurs beyond the single incorporated base. Many approaches can be taken for determining the identity of a terminator, including fluorescence labeling, mass labeling for mass spectrometry, measuring enzyme activity using a protein moiety, and isotope labeling.

Reagents and techniques described herein may be directed to performance of "Next Generation Sequencing." (See, e.g., Srivatsan et al., PLoS Genet 4: e100139 (2008); Rasmussen et al., Nature 463:757-762 (2010); Li et al., Nature 463: 311-317 (2010); Pelak et al., PLoS Genet 6: e1001111 (2010); Ram et al., Syst Biol Reprod Med (57(3):117-118 (2011); McEllistrem, Future Microbiol 4: 857-865 (2009); Lo et al., Clin Chem 55: 607-608 (2009); Robinson, Genome Biol 11:144 (2010); and Araya et al., Trends Biotechnology doi10.1016.j.tibtech.2011.04.003 (2011)). For example, such techniques may involve the fragmentation of a genomic nucleic acid sample followed by parallel sequencing of those fragments and the alignment of the sequenced fragments to reconstruct the original sequence. Here, the genomic nucleic acid of interest is sheared into fragments and "adapters" (short nucleic acids of known sequence) are ligated to the fragments. Adaptor-modified fragments can be enriched via PCR. An adaptor-modified fragment (and amplified copies thereof, if present) may be flowed across a flow cell where the fragments are allowed to hybridize to primers immobilized on the surface of the cell. The fragments are then amplified by isothermal bridge amplification into a cluster consisting of thousands of molecules identical to the original. Sequencing primers can then be hybridized to the ends of one strand of the clusters, reversibly blocked, and labeled nucleotides added. The addition of each particular nucleotide can be identified by the label, then the label can be removed and the nucleotide un-blocked so that another blocked and labeled nucleotide can be added to identify the next position in the nucleic acid sequence. Once the desired number of rounds of addition, detection, and unblocking occur, the resulting sequences can be aligned.

It will be apparent to one of skill in the art that such primers and probes are directly useful as reagents for detecting the SNPs of the disclosed subject matter, and can be incorporated into any kit/system format.

SNP Genotyping Methods

SNP genotyping includes, for example, collecting a biological sample from a human subject (e.g., sample of tissues, cells, fluids, secretions, etc.), isolating nucleic acids (e.g., genomic DNA, mRNA or both) from the cells of the sample, contacting the nucleic acids with one or more primers which specifically hybridize to a region of the isolated nucleic acid containing a target SNP under conditions such that hybridization and amplification of the target nucleic acid region occurs, and determining the nucleotide present at the SNP position of interest, or, in some assays, detecting the presence or absence of an amplification product (assays can be designed so that hybridization and/or amplification will only occur if a particular SNP allele is present or absent). In some assays, the size of the amplification product is detected and compared to the length of a control sample; for example, deletions and insertions can be detected by a change in size of the amplified product compared to a normal genotype.

SNP genotyping is useful for numerous practical applications, as described herein. Examples of such applications include, but are not limited to, SNP-disease association analysis, disease predisposition screening, disease diagnosis, disease prognosis, disease progression monitoring, determining therapeutic strategies based on an individual's genotype ("pharmacogenomics"), developing therapeutic agents based on SNP genotypes associated with a disease or likelihood of responding to a drug, stratifying patient populations for clinical trials of a therapeutic, preventive, or diagnostic agent, and human identification applications such as forensics.

Nucleic acid samples can be genotyped to determine which allele is present at any given SNP position of interest by methods well known in the art. The neighboring sequence can be used to design SNP detection reagents such as oligonucleotide probes, which may optionally be implemented in a kit format. Exemplary SNP genotyping methods are described in Chen et al., "Single nucleotide polymorphism genotyping: biochemistry, protocol, cost and throughput," Pharmacogenomics J 3 (2):77-96 (2003); Kwok et al., "Detection of single nucleotide polymorphisms," Curr Issues Mol Biol 5 (2):43-60 (April 2003); Shi, "Technologies for individual genotyping: detection of genetic polymorphisms in drug targets and disease genes," Am J Pharmacogenomics 2 (3):197-205 (2002); and Kwok, "Methods for genotyping single nucleotide polymorphisms," Annu Rev Genom Hum Genet 2:235-58 (2001). Techniques for high-throughput SNP genotyping are described in Mamellos, "High-throughput SNP analysis for genetic association studies," Curr Opin Drug Disc Devel 6 (3):317-21 (May 2003).

SNP genotyping methods include, but are not limited to, TaqMan® assays, molecular beacon assays, nucleic acid arrays, allele-specific primer extension, allele-specific PCR, arrayed primer extension, homogeneous primer extension assays, primer extension with detection by mass spectrometry, pyrosequencing, multiplex primer extension sorted on genetic arrays, ligation with rolling circle amplification, homogeneous ligation, Oligonucleotide Ligation Assay (OLA: U.S. Pat. No. 4,988,167), multiplex ligation reaction sorted on genetic arrays, restriction-fragment length polymorphism, single base extension-tag assays, denaturing gradient gel electrophoresis, and the Invader assay. Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection.

In one embodiment, SNP genotyping is performed using the TaqMan® assay, which is also known as the 5' nuclease assay (U.S. Pat. Nos. 5,210,015 and 5,538,848). The TaqMan® assay detects the accumulation of a specific amplified product during PCR. The TaqMan® assay utilizes an oligonucleotide probe labeled with a fluorescent reporter dye and a quencher dye. The reporter dye is excited by irradiation at an appropriate wavelength, it transfers energy to the quencher dye in the same probe via a process called fluorescence resonance energy transfer (FRET). When attached to the probe, the excited reporter dye does not emit a signal. The proximity of the quencher dye to the reporter dye in the intact probe maintains a reduced fluorescence for the reporter. The reporter dye and quencher dye may be at the 5' most and the 3' most ends, respectively, or vice versa. Alternatively, the reporter dye may be at the 5' or 3' most end while the quencher dye is attached to an internal nucleotide, or vice versa. In yet another embodiment, both the reporter and the quencher may be attached to internal nucleotides at a distance from each other such that fluorescence of the reporter is reduced.

During PCR, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The DNA polymerase cleaves the probe between the reporter dye and the quencher dye only if the probe hybridizes to the target SNP-containing template which is amplified during PCR, and the probe is designed to hybridize to the target SNP site only if a particular SNP allele is present.

Preferred TaqMan® primer and probe sequences can readily be determined using the SNP and associated nucleic acid sequence information provided herein. A number of computer programs, such as Primer Express (Applied Biosystems, Foster City, Calif.), can be used to rapidly obtain optimal primer/probe sets. These probes and primers can be readily incorporated into a kit format. The disclosed subject matter also includes modifications of the TaqMan® assay well known in the art such as the use of Molecular Beacon probes (U.S. Pat. Nos. 5,118,801 and 5,312,728) and other variant formats (U.S. Pat. Nos. 5,866,336 and 6,117,635).

Another method for genotyping the SNPs can be the use of two oligonucleotide probes in an OLA (see, e.g., U.S. Pat. No. 4,988,617). In this method, one probe hybridizes to a segment of a target nucleic acid with its 3' most end aligned with the SNP site. A second probe hybridizes to an adjacent segment of the target nucleic acid molecule directly 3' to the first probe. The two juxtaposed probes hybridize to the target nucleic acid molecule, and are ligated in the presence of a linking agent such as a ligase if there is perfect complementarity between the 3' most nucleotide of the first probe with the SNP site. If there is a mismatch, ligation would not occur. After the reaction, the ligated probes are separated from the target nucleic acid molecule, and detected as indicators of the presence of a SNP.

The following patents, patent applications, and published international patent applications, which are all hereby incorporated by reference, provide additional information pertaining to techniques for carrying out various types of Oligonucleotide Ligation Assay (OLA). The following U.S. patents describe OLA strategies for performing SNP detection: U.S. Pat. Nos. 6,027,889; 6,268,148; 5,494,810; 5,830,711 and 6,054,564. WO 97/31256 and WO 00/56927 describe OLA strategies for performing SNP detection using universal arrays, where a zipcode sequence can be introduced into one of the hybridization probes, and the resulting product, or amplified product, hybridized to a universal zip code array. U.S. application Ser. No. 01/17,329 (and Ser. No. 09/584,905) describes OLA (or LDR) followed by PCR, where zipcodes are incorporated into OLA probes, and amplified PCR products are determined by electrophoretic or universal zipcode array readout. U.S. applications 60/427,818, 60/445,636, and 60/445,494 describe SNPlex methods and software for multiplexed SNP detection using OLA followed by PCR, where zipcodes are incorporated into OLA probes, and amplified PCR products are hybridized with a zipchute reagent, and the identity of the SNP determined from electrophoretic readout of the zipchute. In some embodiments, OLA is carried out prior to PCR (or another method of nucleic acid amplification). In other embodiments, PCR (or another method of nucleic acid amplification) is carried out prior to OLA.

Another method for SNP genotyping is based on mass spectrometry. Mass spectrometry takes advantage of the unique mass of each of the four nucleotides of DNA. SNPs can be unambiguously genotyped by mass spectrometry by measuring the differences in the mass of nucleic acids having alternative SNP alleles. MALDI-TOF (Matrix Assisted Laser Desorption Ionization-Time of Flight) mass spectrometry technology is preferred for extremely precise determinations of molecular mass, such as SNPs. Numerous approaches to SNP analysis have been developed based on mass spectrometry. Preferred mass spectrometry-based methods of SNP genotyping include primer extension assays, which can also be utilized in combination with other approaches, such as traditional gel-based formats and microarrays.

Typically, a mass spectrometry with primer extension assay involves designing and annealing a primer to a template PCR amplicon upstream (5') from a target SNP position. A mix of dideoxynucleotide triphosphates (ddNTPs) and/or deoxynucleotide triphosphates (dNTPs) are added to a reaction mixture containing template (e.g., a SNP-containing nucleic acid molecule which has typically been amplified, such as by PCR), primer, and DNA polymerase. Extension of the primer terminates at the first position in the template where a nucleotide complementary to one of the ddNTPs in the mix occurs. The primer can be either immediately adjacent (i.e., the nucleotide at the 3' end of the primer hybridizes to the nucleotide next to the target SNP site) or two or more nucleotides removed from the SNP position. If the primer is several nucleotides removed from the target SNP position, the only limitation is that the template sequence between the 3' end of the primer and the SNP position cannot contain a nucleotide of the same type as the one to be detected, or this will cause premature termination of the extension primer. Alternatively, if all four ddNTPs alone, with no dNTPs, are added to the reaction mixture, the primer will always be extended by only one nucleotide, corresponding to the target SNP position. In this instance, primers are designed to bind one nucleotide upstream from the SNP position (i.e., the nucleotide at the 3' end of the primer hybridizes to the nucleotide that is immediately adjacent to the target SNP site on the 5' side of the target SNP site). Extension by only one nucleotide is preferable, as it minimizes the overall mass of the extended primer, thereby increasing the resolution of mass differences between alternative SNP nucleotides. Furthermore, mass-tagged ddNTPs can be employed in the primer extension reactions in place of unmodified ddNTPs. This increases the mass difference between primers extended with these ddNTPs, thereby providing increased sensitivity and accuracy, and is particularly useful for typing heterozygous base positions.

Primer extension assays may be used in conjunction with MALDI-TOF mass spectrometry for SNP genotyping, see, e.g., Wise et al., "A standard protocol for single nucleotide primer extension in the human genome using matrix-assisted laser desorption/ionization time-of-flight mass spectrometry," Rapid Comm. Mass Spect. 17 (11):1195-202 (2003).

SNPs can also be scored by direct DNA sequencing. A variety of automated sequencing procedures can be utilized (e.g., Biotechniques 19:448 (1995)), including sequencing by mass spectrometry. See, e.g., PCT International Publication No. WO 94/16101; Cohen et al., Adv Chromatogr 36:127-162 (1996); and Griffin et al, Appl Biochem Biotechnol 38:147-159 (1993). The nucleic acid sequences of the disclosed subject matter enable one of ordinary skill in the art to readily design sequencing primers for such automated sequencing procedures. Commercial instrumentation, such as the Applied Biosystems 377, 3100, 3700, 3730, and 3730×1 DNA Analyzers (Foster City, Calif.), is commonly used in the art for automated sequencing.

Other methods that can be used to genotype the SNPs of the disclosed subject matter include single-strand conformational polymorphism (SSCP), and denaturing gradient gel electrophoresis (DGGE). Myers et al., Nature 313:495 (1985). SSCP identifies base differences by alteration in electrophoretic migration of single stranded PCR products, as described in Orita et al., Proc. Nat. Acad. Single-stranded PCR products can be generated by heating or otherwise denaturing double stranded PCR products. Single-stranded nucleic acids may refold or form secondary structures that are partially dependent on the base sequence. The different electrophoretic mobilities of single-stranded amplification products are related to base-sequence differences at SNP positions. DGGE differentiates SNP alleles based on the different sequence-dependent stabilities and melting properties inherent in polymorphic DNA and the corresponding differences in electrophoretic migration patterns in a denaturing gradient gel. PCR Technology: Principles and Applications for DNA Amplification Chapter 7, Erlich, ed., W.H. Freeman and Co, N.Y. (1992).

Sequence-specific ribozymes (U.S. Pat. No. 5,498,531) can also be used to score SNPs based on the development or loss of a ribozyme cleavage site. Perfectly matched sequences can be distinguished from mismatched sequences by nuclease cleavage digestion assays or by differences in melting temperature. If the SNP affects a restriction enzyme cleavage site, the SNP can be identified by alterations in restriction enzyme digestion patterns, and the corresponding changes in nucleic acid fragment lengths determined by gel electrophoresis.

SNP Detection Kits and Systems

A person skilled in the art will recognize that, based on the SNP and associated sequence information disclosed herein, detection reagents can be developed and used to assay the SNP of the disclosed subject matter individually or in combination with other SNPs, and such detection reagents can be readily incorporated into one of the established kit or system formats which are well known in the art.

The terms "kits" and "systems," as used herein in the context of SNP detection reagents, are intended to refer to such things as combinations of multiple SNP detection reagents, or one or more SNP detection reagents in combination with one or more other types of elements or components (e.g., other types of biochemical reagents, containers, packages such as packaging intended for commercial sale, substrates to which SNP detection reagents are attached, electronic hardware components, and software recorded on a non-transitory processor-readable medium). Accordingly, the disclosed subject matter further provides SNP detection kits and systems, including but not limited to, packaged probe and primer sets (e.g., TaqMan® probe/primer sets), arrays/microarrays of nucleic acid molecules, and beads that contain one or more probes, primers, or other detection reagents for detecting one or more SNPs of the disclosed subject matter.

The kits/systems can optionally include various electronic hardware components; for example, arrays ("DNA chips") and microfluidic systems ("lab-on-a-chip" systems) provided by various manufacturers typically include hardware components. Other kits/systems (e.g., probe/primer sets) may not include electronic hardware components, but may include, for example, one or more SNP detection reagents (along with, optionally, other biochemical reagents) packaged in one or more containers.

In some embodiments, a SNP detection kit typically contains one or more detection reagents and other components (e.g., a buffer, enzymes such as DNA polymerases or ligases, chain extension nucleotides such as deoxynucleotide triphosphates, and in the case of Sanger-type DNA sequencing reactions, chain terminating nucleotides, positive control sequences, negative control sequences, and the like) necessary to carry out an assay or reaction, such as amplification and/or detection of a SNP-containing nucleic acid molecule.

A kit may further contain instructions for using the kit to detect the SNP-containing nucleic acid molecule of interest. The instructions may include information which allows a user to identify whether an individual having an inflammation-related disorder/disease has genotype-specific differential expression of IL-1, i.e., is a "high" or "low" producer of IL-1, based upon the Composite IL-1 Genetic Patterns disclosed in Table 1, and to decide on an appropriate anti-inflammatory drug or composition (e.g., as disclosed in Table 2 and/or an alternate drug having a similar or identical mode of action as a drug disclosed in Table 2) and at an appropriate dose.

In one embodiment, kits are provided which contain the necessary reagents to carry out one or more assays to detect one or more SNPs disclosed herein. In another embodiment, SNP detection kits/systems are in the form of nucleic acid arrays, or compartmentalized kits, including microfluidic/lab-on-a-chip systems.

SNP detection kits/systems may contain, for example, one or more probes, or pairs of probes, that hybridize to a nucleic acid molecule at or near each target SNP position. Multiple pairs of allele-specific probes may be included in the kit/system to simultaneously assay large numbers of SNPs, at least one of which is the SNP of the disclosed subject matter. In some kits/systems, the allele-specific probes are immobilized to a substrate such as an array or bead.

The terms "arrays," "microarrays," and "DNA chips" are used herein interchangeably to refer to an array of distinct polynucleotides affixed to a substrate, such as glass, plastic, paper, nylon or other type of membrane, filter, chip, or any other suitable solid support. The polynucleotides can be synthesized directly on the substrate, or synthesized separate from the substrate and then affixed to the substrate.

Any number of probes, such as allele-specific probes, may be implemented in an array, and each probe or pair of probes can hybridize to a different SNP position. In the case of polynucleotide probes, they can be synthesized at designated areas (or synthesized separately and then affixed to designated areas) on a substrate using a light-directed chemical process. Each DNA chip can contain, for example, thousands to millions of individual synthetic polynucleotide probes arranged in a grid-like pattern and miniaturized (e.g., to the size of a dime). Preferably, probes are attached to a solid support in an ordered, addressable array.

A SNP detection kit/system can include components that are used to prepare nucleic acids from a test sample for the subsequent amplification and/or detection of a SNP-containing nucleic acid molecule. Such sample preparation components can be used to produce nucleic acid extracts (including DNA and/or RNA), proteins or membrane extracts from any bodily fluids (such as blood, serum, plasma, urine, saliva, phlegm, gastric juices, semen, tears, sweat, etc.), skin, hair, cells (especially nucleated cells), biopsies, buccal swabs or tissue or tumor specimens. Methods of preparing nucleic acids, proteins, and cell extracts are well known in the art and can be readily adapted to obtain a sample that is compatible with the system utilized. Automated sample preparation systems for extracting nucleic acids from a test sample are commercially available, and examples are Qiagen's BioRobot 9600, Applied Biosystems' PRISM 6700 sample preparation system, and Roche Molecular Systems' COBAS AmpliPrep System.

For genotyping SNPs, an exemplary microfluidic system may integrate, for example, nucleic acid amplification, primer extension, capillary electrophoresis, and a detection method such as laser induced fluorescence detection. In an exemplary process for using such an exemplary system, nucleic acid samples are amplified, preferably by PCR. Then, the amplification products are subjected to automated primer extension reactions using ddNTPs (specific fluorescence for each ddNTP) and the appropriate oligonucleotide primers to carry out primer extension reactions which hybridize just upstream of the targeted SNP. Once the extension at the 3' end is completed, the primers are separated from the unincorporated fluorescent ddNTPs by capillary electrophoresis. The separation medium used in capillary electrophoresis can be, for example, polyacrylamide, polyethyleneglycol or dextran. The incorporated ddNTPs in the single nucleotide primer extension products are identified by laser-induced fluorescence detection. Such an exemplary microchip can be used to process, for example, at least 96 to 384 samples, or more, in parallel.

An exemplary kit allows a user to determine whether a subject is predisposed to having an IL-1β-related disorder/would receive a therapeutic benefit from/would be responsive to Isunakinra based upon the human subject's Composite IL-1 Genetic Pattern. The IL-1β-related disorder can be allergic conjunctivitis (AC) and/or dry eye disease. The kit would include instructions indicating that a subject with Composite IL-1 Genetic Pattern 1 or 2 is more likely to be predisposed to having AC and/or dry eye disease that is IL-1 governing and/or would receive a therapeutic benefit from/would be responsive to Isunakinra. On the other hand, the kit would include instructions indicating that a subject with Composite IL-1 Genetic Pattern 3 is less likely to be predisposed to having AC and/or dry eye disease that is IL-1 governing and/or would not receive a therapeutic benefit from/would not be as responsive to Isunakinra when compared to a subject with Composite IL-1 Genetic Pattern 1 or 2.

Reports, Programmed Computers, and Systems

The results of a test (e.g., a genotype determination or identification of a Composite IL-1 Genotype Pattern, as disclosed in Table 1), or an individual's predicted drug responsiveness (e.g., response of a drug disclosed in Table 2 and/or an alternate drug having a mode of action similar to or identical to a drug from Table 2, based upon his/her Composite IL-1 Genotype Pattern) may be referred to herein as a "report". The report may include other information based on assaying the SNPs disclosed herein, alone or in combination with other SNPs, and/or an individual's allele/genotype at the SNPs disclosed herein, alone or in combination with other SNPs, etc.), and/or any other information pertaining to a test.

A tangible report can optionally be generated as part of a testing process (which may be interchangeably referred to herein as "reporting", or as "providing" a report, "producing" a report, or "generating" a report).

Examples of tangible reports may include, but are not limited to, reports in paper (such as computer-generated printouts of test results or hand written reports) or equivalent formats and reports stored on computer readable medium (such as a CD, USB flash drive or other removable storage device, computer hard drive, or computer network server, etc.). Reports, particularly those stored on computer readable medium, can be part of a database, which may optionally be accessible via the interne (such as a database of patient records or genetic information stored on a computer network server, which may be a "secure database" that has security features that limit access to the report, such as to allow only the patient and the patient's medical practitioners to view the report while preventing other unauthorized individuals from viewing the report, for example). In addition to, or as an alternative to, generating a tangible report, reports can also be displayed on a computer screen (or the display of another electronic device or instrument).

In addition to, or as an alternative to, the report may be "intangible" in that it is orally presented to another.

A tangible report may be hand written or may be prepared using a computer.

A report may be provided to the individual who can then implement the information and/or instructions contained therein.

A report may be provided to a health care professional who can then implement the information and/or instructions contained therein and/or instruct the individual (e.g., prescribe and make a recommendation).

A report can include, for example, an individual's predicted drug responsiveness (e.g., to a drug disclosed in Table 2 and/or an alternate drug having a mode of action similar to or identical to a drug from Table 2 based upon his/her Composite IL-1 Genotype Pattern, as disclosed in Table 1), the allele/genotype that an individual carries at the SNP location disclosed herein, and/or his/her Composite IL-1 Genotype Pattern. Thus, for example, the report can include information of medical/biological significance (e.g., drug responsiveness, suggested treatment, and prophylactic methods). The report may just include allele/genotype information and/or a Composite IL-1 Genotype Pattern without including disease risk or other medical/biological significance; thus, the individual viewing the report can use the allele/genotype information and/or Composite IL-1 Genotype Patter to determine the associated disease risk or other medical/biological significance from a source outside of the report itself, such as from a medical practitioner, publication, website, etc., which may optionally be linked to the report such as by a hyperlink.

A report can further be "transmitted" or "communicated" (these terms may be used herein interchangeably), such as to the individual who was tested, a medical practitioner (e.g., a doctor, nurse, clinical laboratory practitioner, genetic counselor, etc.), a healthcare organization, a clinical laboratory, and/or any other party or requester intended to view or possess the report. The act of "transmitting" or "communicating" a report can be by any means known in the art, based on the format of the report. Furthermore, "transmitting" or "communicating" a report can include delivering a report ("pushing") and/or retrieving ("pulling") a report. For example, reports can be transmitted/communicated by various means, including being physically transferred between parties (such as for reports in paper format) such as by being physically delivered from one party to another, or by being transmitted electronically or in signal form (e.g., via e-mail or over the interne, by facsimile, and/or by any wired or wireless communication methods known in the art) such as by being retrieved from a database stored on a computer network server.

Additional teaching relevant to the present invention are described in one or more of the following: U.S. Pat. Nos. 5,686,246, 5,698,399, 5,808,918, 6,108,635, 6,140,047, 6,210,877, 6,251,598, 6,268,142, 6,383,775, 6,437,216, 6,524,795, 6,551,785, 6,558,905, 6,706,478, 6,713,253, 6,720,141, 6,730,476, 6,733,967, 6,746,839, 7,723,028, 7,820,383, 8,101,360, 8,105,775, U.S. 2002-0182612, U.S. 2003-0100031, U.S. 2003-0124524, U.S. 2003-0152947, U.S. 2003-0235890, U.S. 2004-0152124, U.S. 2005-0032077, U.S. 2005-0064453, U.S. 2005-0171338, U.S. 2005-0282198, U.S. 2006-0183161, U.S. 2006-0252050, U.S. 2007-0264645, U.S. 2007-0275104, U.S. 2008-0118920, U.S. 2008-0187920, U.S. 2008-0199865, U.S. 2008-0254476, U.S. 2008-0254477, U.S. 2008-0254478, U.S. 2008-0311581, U.S. 2009-0023147, U.S. 2009-0093396, U.S. 2009-0163460, U.S. 2009-0170105, U.S. 2009-0191564, U.S. 2010-0028893, U.S. 2010-0129798, U.S. 2010-0255475, U.S. 2010-0279280, U.S. 2011-0008906, U.S. 2013-0011841, U.S. 2003-0175764, U.S. 2004-0110168, U.S. 2010-0098775, U.S. 2010-0098809, U.S. 2010-0105038, U.S. 2010-0112570, U.S. 2010-0136561, U.S. 2012-0208187, and U.S. 2013-0337448, each of which is incorporated herein by reference in their entireties.

Definitions

The term "single nucleotide polymorphisms" (SNPs) refers to a variation in the sequence of a gene in the genome of a population that arises as the result of a single base change, such as an insertion, deletion or, a change in a single base. A locus is the site at which divergence occurs. SNPs can result in modified amino acid sequences, altering structure and function of coded protein, and influence the splicing process when present at exon-intron transitions and modify gene transcription when part of promoters. This modification can lead to altered levels of protein expression.

As used herein, the terms "treat," "treating," "treatment," and the like refer to reducing or ameliorating a disorder and/or a symptom associated therewith. It will be appreciated that, although not precluded, treating a disorder or condition does not require that the disorder, condition or symptoms associated therewith be completely eliminated. Treating may include a health care professional or diagnostic scientist making a recommendation to a subject for a desired course of action or treatment regimen, e.g., a prescription.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

As used herein, the terms "drug", "medication", "therapeutic", "active agent", "therapeutic compound", "composition", or "compound" are used interchangeably and refer to any chemical entity, pharmaceutical, drug, biological, botanical, and the like that can be used to treat or prevent a disease, illness, condition, or disorder of bodily function. A drug may comprise both known and potentially therapeutic compounds. A drug may be determined to be therapeutic by screening using the screening known to those having ordinary skill in the art. A "known therapeutic compound", "drug", or "medication" refers to a therapeutic compound that has been shown (e.g., through animal trials or prior experience with administration to humans) to be effective in such treatment. A "therapeutic regimen" relates to a treatment comprising a "drug", "medication", "therapeutic", "active agent", "therapeutic compound", "composition", or "compound" as disclosed herein and/or a treatment comprising behavioral modification by the subject and/or a treatment comprising a surgical means.

As used herein "an aggressive therapeutic regimen comprising a drug that inhibits IL-1β activity" comprises a higher dose (e.g., the dose of a single treatment and/or a daily dose comprising one or more single treatments) of the drug than "a mild therapeutic regimen comprising a drug that inhibits IL-1β activity." The actual dose of the drug is drug-dependent. A skilled artisan having knowledge of the drug would understand what is considered to be a higher dose and what is considered to be lower dose of the drug.

Unless otherwise defined, all technical and scientific terms used herein have the same meaning as commonly understood by one of ordinary skill in the art to which this invention belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about." As used herein, the term "plurality" is meant more than one, i.e., 2, 3, 4, 5, 6, 7, 8, 9, 10, 100, 1,000, 10,000, 100,000 or more and any number in between.

Although methods and materials similar or equivalent to those described herein can be used in the practice or testing of the present invention, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting.

EXAMPLES

Example 1

Individual Patient Responses to an Inflammatory Challenge is Dependent Upon His/Her Composite IL-1 Genotype Pattern In this example, subjects' inflammatory responses to a standard activator of inflammation were correlated with their Composite IL-1 Genotype Pattern. Here, 645 female subjects were screened for entrance criteria: (1) between the ages of 20 to 35 and (2) Fitzpatrick skin tone I to III. Subjects were genotyped and twenty to thirty subjects for each of Composite IL-1 Genotype Patterns 1 to 3 were selected for inclusion in the test. The selected subjects were exposed to an inflammatory challenge, i.e., ultraviolet (UV) irradiation (a standard activator of inflammation). Subjects were exposed to increasing doses of UV irradiation and the minimal UV dose needed to produce clinically measurable inflammation of the skin was determined by standardized examiners and independently assessed by spectrophotometric readings of the skin. The scores for each individual were expressed as minimal erythemal dose (MED). All measurements were performed by trained examiners who were blinded to the subject's genotype. Then, each subject's inflammatory response was correlated with her Composite IL-1 Genotype Pattern. Results are shown below in Table 3.

TABLE 3

| Genotype Pattern | Number of Subjects | Mean UV Dose to Cause Inflammation |
|---|---|---|
| 1 | 17 | 38.82 (8.06) |
| 2 | 31 | 38.45 (6.17) |
| 3 | 20 | 48.15 (10.45) |
|   |   | ANOVA p = 0.013 |
| 1 + 2 | 48 | 38.58 (6.81) |
|   |   | Pattern 1 + 2 vs. 3: p = 0.003 |

Subjects with Composite IL-1 Genotype Patterns 1 and 2 (the "high IL-1β producers") developed a clinically measurable inflammatory response at lower challenge doses of UV irradiation when compared to subjects with Pattern 3 (the "low IL-1β producers"). In skin biopsies following UV irradiation, subjects with Patterns 1 and 2 had higher mRNA expression of the IL1A gene when compared to subjects with Pattern 3 (p<0.0001). Subjects with Pattern 2 had higher mRNA expression of the IL1B, IL6, and MMP9 genes when compared to subjects with Pattern 3 (p<0.0001). Together, the high IL-1β producers experienced inflammation at lower UV doses when compared to the low IL-1β producers.

These data suggest that individuals should have differential responses to drugs targeting IL-1α and/or IL-1β based upon his/her Composite IL-1 Genotype Patterns.

Example 2

Individual Patient Responses to a IL-1 Blocking Drug is Dependent Upon His/Her Composite IL-1 Genotype Pattern In this example, subjects' responses to a recombinant IL-1 receptor antagonist (IL-1RA) were correlated with their Composite IL-1 Genotype Pattern. IL-1 biological activity is a function of the balance between the pro-inflammatory agonists IL-1α and IL-1β and the anti-inflammatory protein, IL-1RA. Human recombinant IL-1RA is approved for clinical use for treating multiple diseases, including rheumatoid arthritis.

In a randomized controlled trial for treating rheumatoid arthritis, subjects were administered the recombinant IL-1RA anakinra (150 mg/day) or a placebo. A positive response was defined as a reduction of at least 50% in the number of swollen joints by week 24 (American College of Rheumatology's 50% response; $ACR_{50}$). The subjects' positive response rate to anakinra administration was 48% (44 positive responses among the 91 subjects); this positive response rate to anakinra was not significantly different from the positive response rate to placebo administration. See, FIG. 2.

Figure 2:
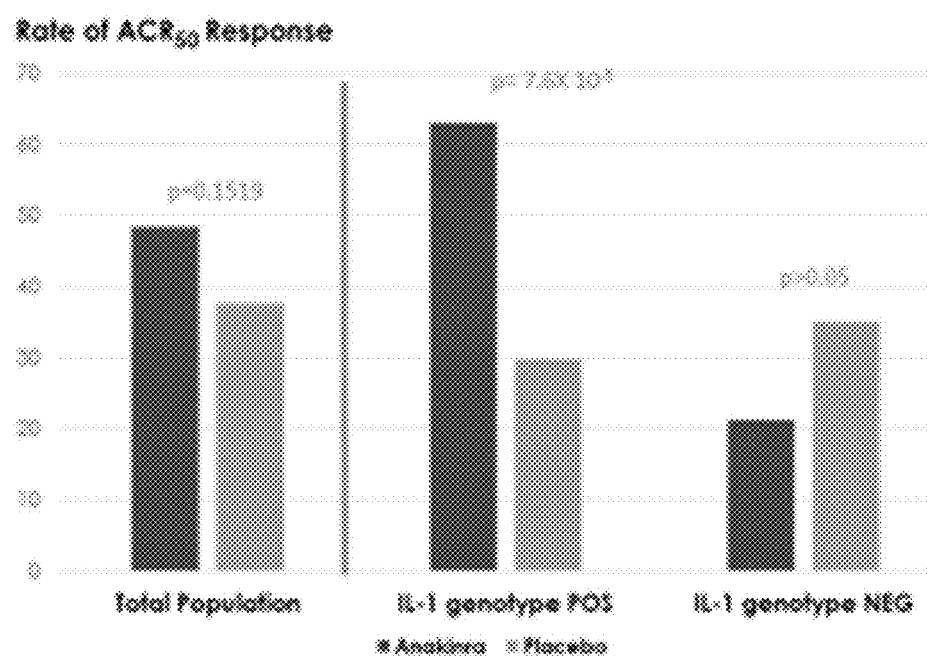
FIG. 2 is a chart showing the clinical response of rheumatoid arthritis patients to an IL-1-blocking drug based upon the patient's Composite IL-1 Genotype Pattern.

Patients were then stratified by the three Composite IL-1 Genotype Patterns. Subjects with Pattern 1 had a 63% positive response rate to anakinra whereas subjects with either Pattern 2 or 3 had a 22% positive response rate. In FIG. 2, subjects with Pattern 1 are identified as "IL-1 genotype POS" and subjects with Patterns 2 or 3 are identified as "IL-1 genotype NEG." For subjects with Pattern 1, the improved positive response rates for subjects administered anakinra versus placebo was highly significant (p=0.000076). On the other hand, there was no difference in positive response rates for subjects with Pattern 2 or 3 between those who were administered anakinra versus placebo.

In conclusion, the herein-disclosed three functional Composite IL-1 Genotype Patterns differentiate which rheumatoid arthritis patients are likely to have a strong favorable response and which are unlikely to have a clinically meaningful response to the FDA-approved recombinant IL-1RA drug which blocks IL-1 biological activity.

Example 3

Individual Patient Responses to a Botanical Composition that Reduces IL-1 Expression is Dependent Upon His/Her Composite IL-1 Genotype Pattern In this example, subjects' responses to an IL-1-inhibiting botanical composition were correlated with their Composite IL-1 Genotype Pattern. A composition of botanicals was developed which has the ability to inhibit IL-1β gene expression in human mononuclear cells. Selected candidate ingredients were also screened for inhibition of mediator production downstream of IL-1β. The primary IL-1-inhibiting ingredient was a rose hips extract. Four secondary ingredients were selected for downstream mediator inhibition.

Overtly healthy adult subjects with CRP levels of 2 mg/L or greater qualified for participation in this randomized, controlled clinical trial. Subjects were genotyped for composite IL-1 genetic patterns. Prior to randomization, subjects with Pattern 1 or 2 were sorted into the "Positive for IL-1" genotype category and subjects with Pattern 3 were sorted into the "Negative for IL-1" genotype category. Within each of the two genotype categories, subjects were randomized to receive either the botanicals or a placebo.

Subjects consumed their assigned product daily for 12 weeks. All subjects were monitored at baseline and every two weeks for mononuclear cell peripheral blood mononuclear cell production of IL-1β and for blood CRP levels.

Subjects in the Positive for IL-1 category and who received the botanical composition had a mean reduction from baseline in IL-1 expression of 61.2% at week 12, whereas subjects in this category who received the placebo had no change from baseline. This difference between groups was statistically significant (p<0.001). Subjects in the Negative for IL-1 category and who received the botanical composition had a mean reduction from baseline in IL-1 expression of 43.8% at week 12; this reduction was significantly different from the subjects in this category who received the placebo (p<0.05). Subjects in the Positive for IL-1 category had a significantly greater reduction in IL-1 expression following receipt of the botanical composition when compared to subjects in the Negative for IL-1 category (p=0.012), as measured by percentage of subjects in each category with a reduction in IL-1 expression of greater than 30% from baseline.

A reduction of blood CRP greater than 30% from baseline was observed in 40% of the subjects in the Positive for IL-1 category who received the botanical composition whereas such CRP reduction was observed in only 10.5% of the subjects in the Negative for IL-1 category who received the botanical composition (p=0.03).

Example 4

Use of the Composite IL-1 Genotype Patterns with an Injectable Composition for Treating Type 1 Diabetes Mellitus In this example, subjects' responses to a subcutaneous composition for treating Type 1 Diabetes Mellitus will be correlated with their Composite IL-1 Genotype Pattern. Here, subjects afflicted with Type 1 Diabetes Mellitus will be randomized and one group will be subcutaneously injected once every four weeks with Gevokizumab (manufactured by Xoma/Servier) formulated at 0.3 mg/kg and another group will be administered a placebo. Subjects will later have their therapeutic response quantified. Subjects will be genotyped and stratified by the three Composite IL-1 Genotype Patterns. Finally, correlations among treatment groups and Composite IL-1 Genotype Patterns will be calculated and positive response rates for each Pattern will be determined.

Example 5

Use of the Composite IL-1 Genotype Patterns with a Topical Ophthalmic Anti-Inflammatory Composition In this example, subjects' responses to a topical ophthalmic anti-inflammatory will be correlated with their Composite IL-1 Genotype Pattern. Here, subjects afflicted with dry eye disease or allergic conjunctivitis (AC) will be randomized and one group will be administered three times per day Isunakinra (manufactured by Eleven Biotherapeutics) formulated at 5 mg/ml or 20 mg/ml and another group will be administered a placebo. Subjects will later have their therapeutic response quantified. Subjects will be genotyped and stratified by the three Composite IL-1 Genotype Patterns. Finally, correlations among treatment groups and Composite IL-1 Genotype Patterns will be calculated and positive response rates for each Pattern will be determined.

Example 6

Use of the Composite IL-1 Genotype Patterns for Revaluating a Clinical Trial that Fails to Reach its Primary Endpoint In this example, a Phase 3 clinical study evaluating the effectiveness of Gevokizumab (manufactured by Xoma/Servier) on treating Behçet's Disease failed to reach its primary endpoint. In this Phase 3 study, subjects who received a placebo were compared to subjects who received Gevokizumab. In this example, subjects who were enrolled and completed the Phase 3 clinical study will be genotyped and stratified by the three Composite IL-1 Genotype Patterns. For each Composite IL-1 Genotype Pattern, responses of subjects who received Gevokizumab will be compared to subjects who received placebo. Additionally, responses to Gevokizumab for subjects of each Composite IL-1 Genotype Patterns will be compared. By reevaluating the study data, it may be possible to determine that subjects in certain Composite IL-1 Genotype Patterns had reached their primary endpoints whereas subjects in other Composite IL-1 Genotype Patterns did not. Such information will allow the development and the targeted use of individualized therapies to obtain effective and safe treatment.

Example 7

Use of the Composite IL-1 Genotype Patterns with an Oral Anti Osteoarthritis Composition In this example, subjects' responses to an oral anti-osteoarthritis drug will be correlated with their Composite IL-1 Genotype Pattern. Here, subjects afflicted with knee osteoarthritis will be randomized and one group will be administered diacerein (manufactured by TWI Pharmaceuticals) once or twice per day formulated at 50 mg per tablet and another group will be administered a placebo. Subjects will later have their therapeutic response quantified. Before or after randomization or before or after response quantification, subjects will be genotyped and stratified by the three Composite IL-1 Genotype Patterns. Finally, correlations among treatment groups and Composite IL-1 Genotype Patterns will be calculated and positive response rates for each Pattern will be determined.

What is claimed is:

1. A method of treating a human subject with elevated IL-1β, comprising steps of:
   (a) selecting a human subject suspected of having, or at risk for elevated IL-1β;
   (b) obtaining an isolated nucleic acid from a biological sample from the human subject;
   (c) detecting the single nucleotide polymorphism (SNP) alleles in the isolated nucleic acid for each of the IL1B (−511) rs16944 C>T polymorphic locus, the IL1B (−1464) rs1143623 G>C polymorphic locus, the IL1B (−3737) rs4848306 C>T polymorphic locus, the ILIA (+4845) rs17561G>T polymorphic locus and the IL1B (+3954) rs1143634 C>T polymorphic locus;
   (d) determining that the human subject has a positive IL-1 genotype pattern when the IL-1 genotype pattern obtained in (c) matches an IL-1 genotype pattern that is selected from the group consisting of:
   (i) CC at rs16944, GG at rs1143623 and CT at rs4848306 and any allele at the rs17561 and rs1143634 loci,
   (ii) CT at rs16944, GC at rs1143623 and CC at rs4848306 and any allele at the rs17561 and rs1143634 loci,
   (iii) CC at rs16944, GG at rs1143623 and CC at rs4848306 and any allele at the rs17561 and rs1143634 loci,
   (iv) CT at rs16944, GG at rs1143623 and CC at rs4848306 and any allele at the rs17561 and rs1143634 loci,
   (v) CC at rs16944, GG at rs1143623 and TT at rs4848306 and any allele at the rs17561 and rs1143634 loci,
   (vi) CT at rs16944, GC at rs1143623, CT at rs4848306, TT or TG at rs17561 and TT or TC at rs1143634,
   (vii) CT at rs16944, GG at rs1143623, CT at rs4848306, TT or TG at rs17561 and TT or TC at rs1143634,
   (viii) TT at rs16944, CC at rs1143623, CC at rs4848306, TT or TG at rs17561, and TT or TC at rs1143634,
   (ix) TT at rs16944, CG at rs1143623, CC at rs4848306, TT or TG at rs17561, and TT or TC at rs1143634, and
   (x) TT at rs16944, GG at rs1143623, CC at rs4848306, TT or TG at rs17561, and TT or TC at rs1143634;
   (e) diagnosing the human subject as having elevated IL-1β when the human subject has a positive IL-1 genotype pattern determined in step (d); and
   (f) administering a drug that inhibits IL-1β activity to the human subject diagnosed in step (e).

2. The method of claim 1, wherein the human subject has, or is at risk of developing a disease selected from the group consisting of cardiovascular disease, systemic inflammatory response, general inflammatory response, Alzheimer's disease, arthritis, asthma, atherosclerosis, autoimmune myocarditis, congestive heart failure, coronary artery disease, myocardial infarction, acute ischemic stroke, restenosis following coronary stenting, venous thrombosis, diabetes, gastrointestinal inflammatory disease, gastric ulcers, hepatic inflammation, HIV infection, multiple sclerosis, nephropathy, neurodegenerative disease, allergic conjunctivitis, dry eye syndrome, osteoporosis, chronic otitis media, pancreatitis, periodontitis, per-implantitis, excessive bone resorption due to excessive tooth movement, restenosis, thyroiditis, alopecia areata, Graves' disease, psoriasis, systemic lupus erythematosus, systemic sclerosis, and tissue transplant rejection.

3. The method of claim 1, wherein the drug that inhibits IL-1β activity comprises a drug that binds directly to IL-1α or IL-1β to block binding to the IL-1 Receptor, an IL-1 Receptor Antagonist or an inflammasome modulator.

4. A method for determining whether a human subject would receive a therapeutic benefit from a drug that inhibits IL-1β activity comprising steps of:
   (a) obtaining an isolated nucleic acid from a biological sample from the human subject;
   (b) detecting the single nucleotide polymorphism (SNP) alleles in the isolated nucleic acid for each of the IL1B (−511) rs16944 C>T polymorphic locus, the IL1B (−1464) rs1143623 G>C polymorphic locus, and the IL1B (−3737) rs4848306 C>T polymorphic locus the ILIA (+4845) rs17561G>T polymorphic locus and the IL1B (+3954) rs1143634 C>T polymorphic locus; and
   (c) determining that the human subject has a positive IL-1 genotype pattern when the IL-1 genotype pattern obtained in (b) matches an IL-1 genotype pattern that is selected from the group consisting of:
   (i) CC at rs16944, GG at rs1143623 and CT at rs4848306 and any allele at the rs17561 and rs1143634 loci,
   (ii) CT at rs16944, GC at rs1143623 and CC at rs4848306 and any allele at the rs17561 and rs1143634 loci,
   (iii) CC at rs16944, GG at rs1143623 and CC at rs4848306 and any allele at the rs17561 and rs1143634 loci,
   (iv) CT at rs16944, GG at rs1143623 and CC at rs4848306 and any allele at the rs17561 and rs1143634 loci,
   (v) CC at rs16944, GG at rs1143623 and TT at rs4848306 and any allele at the rs17561 and rs1143634 loci,
   (vi) CT at rs16944, GC at rs1143623, CT at rs4848306, TT or TG at rs17561 and TT or TC at rs1143634,
   (vii) CT at rs16944, GG at rs1143623, CT at rs4848306, TT or TG at rs17561 and TT or TC at rs1143634,
   (viii) TT at rs16944, CC at rs1143623, CC at rs4848306, TT or TG at rs17561, and TT or TC at rs1143634,
   (ix) TT at rs16944, CG at rs1143623, CC at rs4848306, TT or TG at rs17561, and TT or TC at rs1143634, and
   (x) TT at rs16944, GG at rs1143623, CC at rs4848306, TT or TG at rs17561, and TT or TC at rs1143634;
   (d) diagnosing the human subject as having elevated IL-1 (3 when the human subject has a positive IL-1 genotype pattern determined in step (c); and
   (e) administering a drug that inhibits IL-1β activity to the human subject diagnosed in step (d).

5. The method of claim 4, wherein the drug that inhibits IL-1β activity is a drug that binds directly to IL-1α or IL-1β to block binding to the IL-1 Receptor, an IL-1 Receptor Antagonist or an inflammasome modulator.

6. The method of claim 1, wherein the human subject has, or is at risk of developing allergic conjunctivitis (AC) and/or dry eye disease.

7. The method of claim 3, wherein the inflammasome modulator is selected from the group consisting of Opsona, RON-2315, Diacerein, AC-701, Sairei-To, binimetinib, Can-04, Rilonacept, Tadekinig-alpha, XL-130, Givinostat and Ammonium trichlorotellurate.

8. The method of claim 3, wherein the inflammasome modulator is a small molecule.

9. The method of claim 8, wherein the small molecule is selected from the group consisting of Givinostat, Diacerein, Ammonium trichlorotellurate and binimetinib.

10. The method of claim 4, wherein the inflammation related disease or disorder is selected from the group consisting of cardiovascular disease, systemic inflammatory response, general inflammatory response, Alzheimer's disease, arthritis, asthma, atherosclerosis, autoimmune myocarditis, congestive heart failure, coronary artery disease, myocardial infarction, acute ischemic stroke, restenosis following coronary stenting, venous thrombosis, diabetes, gastrointestinal inflammatory disease, gastric ulcers, hepatic inflammation, HIV infection, multiple sclerosis, nephropathy, neurodegenerative disease, allergic conjunctivitis, dry eye syndrome, osteoporosis, chronic otitis media, pancreatitis, periodontitis, per-implantitis, excessive bone resorption due to excessive tooth movement, restenosis, thyroiditis, alopecia areata, Graves' disease, psoriasis, systemic lupus erythematosus, systemic sclerosis, and tissue transplant rejection.

11. The method of claim 4, wherein the subject has, or is at risk of developing allergic conjunctivitis (AC) and/or dry eye disease.

12. The method of claim 5, wherein the inflammasome modulator is a small molecule.

13. The method of claim 12, wherein the small molecule is selected from the group consisting of Givinostat, Diacerein, Ammonium trichlorotellurate and binimetinib.

\* \* \* \* \*

UNITED STATES PATENT AND TRADEMARK OFFICE
CERTIFICATE OF CORRECTION

PATENT NO. : 10,894,985 B2  
APPLICATION NO. : 15/404733  
DATED : January 19, 2021  
INVENTOR(S) : Lynn Doucette-Stamm et al.

Page 1 of 1

It is certified that error appears in the above-identified patent and that said Letters Patent is hereby corrected as shown below:

In the Claims

At Column 44, Claim number 4, Line 56:
"(d) diagnosing the human subject as having elevated IL-1"
Should read:
-- (d) diagnosing the human subject as having elevated --

At Column 44, Claim number 4, Line 57:
"(3 when the human subject has a positive IL-1 genotype"
Should read:
-- IL-1β when the human subject has a positive IL-1 genotype --

Signed and Sealed this  
Fifteenth Day of June, 2021

Drew Hirshfeld  
*Performing the Functions and Duties of the*  
*Under Secretary of Commerce for Intellectual Property and*  
*Director of the United States Patent and Trademark Office*